US010141515B2

(12) United States Patent
Noh et al.

(10) Patent No.: US 10,141,515 B2
(45) Date of Patent: Nov. 27, 2018

(54) SPACE-THROUGH CHARGE TRANSFER COMPOUND, AND ORGANIC LIGHT EMITTING DIODE AND DISPLAY DEVICE USING THE SAME

(71) Applicant: LG Display Co., Ltd., Seoul (KR)

(72) Inventors: Hyo-Jin Noh, Paju-si (KR); Kyung-Jin Yoon, Goyang-si (KR); Dae-Wi Yoon, Paju-si (KR); In-Ae Shin, Paju-si (KR); Jun-Yun Kim, Goyang-si (KR)

(73) Assignee: LG Display Co., Ltd., Seoul (KR)

( * ) Notice: Subject to any disclaimer, the term of this patent is extended or adjusted under 35 U.S.C. 154(b) by 510 days.

(21) Appl. No.: 14/885,707

(22) Filed: Oct. 16, 2015

(65) Prior Publication Data

US 2016/0111650 A1 Apr. 21, 2016

(30) Foreign Application Priority Data

Oct. 17, 2014 (KR) ........................ 10-2014-0140971
Sep. 11, 2015 (KR) ........................ 10-2015-0129084

(51) Int. Cl.

| | |
|---|---|
| ***H01L 51/00*** | (2006.01) |
| ***C09K 11/06*** | (2006.01) |
| ***H01L 51/50*** | (2006.01) |
| ***C07D 213/38*** | (2006.01) |
| ***C07D 235/18*** | (2006.01) |
| ***C07D 401/10*** | (2006.01) |

(Continued)

(52) U.S. Cl.
CPC ........ *H01L 51/0058* (2013.01); *C07D 213/38* (2013.01); *C07D 235/18* (2013.01); *C07D 401/10* (2013.01); *C07D 403/10* (2013.01); *C09K 11/025* (2013.01); *C09K 11/06* (2013.01); *H01L 27/3258* (2013.01); *H01L 51/005* (2013.01); *H01L 51/006* (2013.01); *H01L 51/0052* (2013.01); *H01L 51/0061* (2013.01); *H01L 51/0067* (2013.01); *H01L 51/0072* (2013.01); *H01L 51/5012* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *H01L 51/5004* (2013.01); *H01L 51/5016* (2013.01); *H01L 2251/552* (2013.01)

(58) Field of Classification Search
None
See application file for complete search history.

(56) References Cited

FOREIGN PATENT DOCUMENTS

| | | | |
|---|---|---|---|
| JP | 2012-167058 A | | 9/2012 |
| KR | 10-2015-0002417 A | | 1/2015 |
| KR | 10-2015-0006374 | * | 1/2015 |

OTHER PUBLICATIONS

Machine English translation of KR 10-2015-0006374. Mar. 22, 2018.*

(Continued)

*Primary Examiner* — Jay Yang
(74) *Attorney, Agent, or Firm* — Fenwick & West LLP

(57) ABSTRACT

Discussed is a space-through charge transfer compound including a naphthalene core; an electron donor moiety selected from carbazole and phenylcarbazole; and an electron acceptor moiety selected from pyridine, diazine, triazole, and phenyl benzodiazole, wherein the electron donor moiety and the electron acceptor moiety are combined to first and eighth positions of the naphthalene core with a benzene linker, respectively.

19 Claims, 5 Drawing Sheets

(51) Int. Cl.

| | |
|---|---|
| ***C07D 403/10*** | (2006.01) |
| ***C09K 11/02*** | (2006.01) |
| ***H01L 27/32*** | (2006.01) |

(56) References Cited

OTHER PUBLICATIONS

European Extended Search Report, European Application No. 15188932.6, dated Feb. 18, 2016, 8 pages.

Hu, J-H. et al., "Excimer-Emitting Single Molecules with Stacked π-Conjugated Groups Covalently Linked at the 1,8-Positions of Naphthalene for Highly Efficient Blue and Green OLEDs," Journal of Materials Chemistry, C: Materials for Optical and Electronic Devices, Apr. 2013, 2 pages, vol. 1, No. 24.

* cited by examiner

SPACE-THROUGH CHARGE TRANSFER COMPOUND, AND ORGANIC LIGHT EMITTING DIODE AND DISPLAY DEVICE USING THE SAME

CROSS-REFERENCE TO RELATED APPLICATIONS

This application claims priority to and the benefit of Republic of Korea Patent Application No. 10-2014-0140971 filed on Oct. 17, 2014, and Republic of Korea Patent Application No. 10-2015-0129084 filed on Sep. 11, 2015, all of which are hereby incorporated by reference in their entirety.

BACKGROUND OF THE INVENTION

Field of the Invention

Embodiments of the invention relate to an organic light emitting diode (OLED) and more particularly to a space-through charge transfer compound having excellent emitting efficiency and an OLED and a display device using the space-through charge transfer compound.

Discussion of the Related Art

The requirements of the large-size display device have led to developments in flat panel display devices as an image displaying device. Among the flat panel display devices, the OLED has rapidly developed.

In the OLED, when the electron and the hole from a cathode, which serves as an electron-injecting electrode, and an anode, which serves as a hole-injecting electrode, are injected into an emitting material layer, the electron and the hole are combined and become extinct such that the light is emitted from the OLED. A flexible substrate, for example, a plastic substrate, can be used as a base substrate for the OLED, and the OLED has excellent characteristics of driving voltage, power consumption and color purity.

The OLED includes a first electrode as an anode on a substrate, a second electrode as a cathode facing the first electrode and an organic emitting layer therebetween.

To improve the emitting efficiency, the organic emitting layer may include a hole injection layer (HIL), a hole transporting layer (HTL), an emitting material layer (EML), an electron transporting layer (HTL) and an electron injection layer (EIL) sequentially stacked on the first electrode.

The hole is transferred into the EML from the first electrode through the HIL and the HTL, and the electron is transferred into the EML from the second electrode through the EIL and the ETL.

The electron and the hole are combined in the EML to generated excitons, and the excitons are transited from an excited state to a ground state such the light is emitted.

The External quantum efficiency of the emitting material for the EML can be expressed by the following equation:

$$\eta_{ext}=\eta_{int}\times\Gamma\times\Phi\times\eta_{out\text{-}coupling}$$

In the above equation, "$\eta_{int}$" is the internal quantum efficiency, "Γ" is the charge balance factor, "Φ" is the radiative quantum efficiency, and "$\eta_{out\text{-}coupling}$" is the out-coupling efficiency.

The charge balance factor "Γ" means a balance between the hole and the electron when generating the exciton. Generally, assuming 1:1 matching of the hole and the electrode, the charge balance factor has a value of "1". The radiative quantum efficiency "Φ" is a value regarding an effective emitting efficiency of the emitting material. In the host-dopant system, the radiative quantum efficiency depends on a fluorescent quantum efficiency of the dopant.

The internal quantum efficiency "$\eta_{int}$" is a ratio of the excitons generating the light to the excitons generated by the combination of the hole and the electron. In the fluorescent compound, a maximum value of the internal quantum efficiency is 0.25. When the hole and the electron are combined to generate the exciton, a ratio of the singlet excitons to the triplet excitons is 1:3 according to the spin structure. However, in the fluorescent compound, only the singlet excitons excluding the triplet excitons are engaged in the emission.

The out-coupling efficiency "$\eta_{out\text{-}coupling}$" is a ratio of the light emitted from the display device to the light emitted from the EML. When the isotropic compounds are deposited in a thermal evaporation method to form a thin film, the emitting materials are randomly oriented. In this instance, the out-coupling efficiency of the display device may be assumed as 0.2.

Accordingly, the maximum emitting efficiency of the OLED including the fluorescent compound as the emitting material is less than approximately 5%.

To overcome the disadvantage of the emitting efficiency of the fluorescent compound, the phosphorescent compound, where both the singlet excitons and the triplet excitons are engaged in the emission, has been developed for the OLED.

The red and green phosphorescent compound having a relatively high efficiency are introduced and developed. However, there is no blue phosphorescent compound meeting the requirements in the emitting efficiency and the reliability.

SUMMARY OF THE INVENTION

Accordingly, the embodiment of the invention is directed to a space-through charge transfer compound and an OLED and a display device using the same that substantially obviate one or more of the problems due to limitations and disadvantages of the related art.

An object of the embodiment of the invention is to provide a space-through charge transfer compound having high emitting efficiency.

Another object of the embodiment of the invention is to provide an OLED and a display device having an improved emission efficiency.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the embodiments of the invention, as embodied and broadly described herein, an aspect of an embodiment of the invention provides a space-through charge transfer compound including a naphthalene core; an electron donor moiety selected from carbazole and phenylcarbazole; and an electron acceptor moiety selected from pyridine, diazine, triazole and phenyl benzodiazole, wherein the electron donor moiety and the electron acceptor moiety are combined to first and eighth positions of the naphthalene core with a benzene linker, respectively.

In another aspect of the embodiment of the invention, provided is a space-through charge transfer compound of Formula 1:

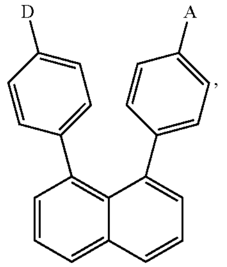

wherein D is selected from

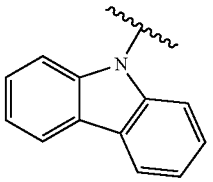
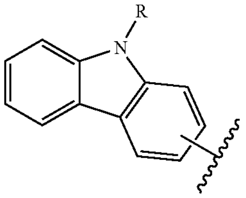
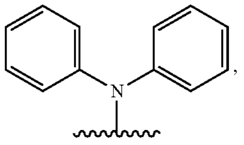

and A is selected from

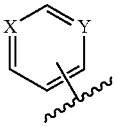
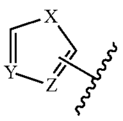
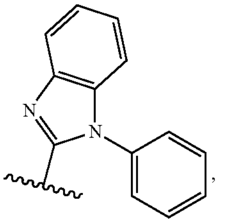

wherein R is selected from hydrogen, C1~C8 alkyl and C6~C20 aryl, and wherein X, Y, Z are independently selected from carbon and nitrogen, and at least one selected from X and Y is nitrogen.

In another aspect of the embodiment of the invention provided is an organic light emitting diode including a first electrode; a second electrode facing the first electrode; and an organic emitting layer between the first and second electrodes and including a space-through charge transfer compound, wherein the space-through charge transfer compound includes a naphthalene core, an electron donor moiety selected from carbazole and phenylcarbazole, and an electron acceptor moiety selected from pyridine, diazine, triazole, and phenyl benzodiazole, and wherein the electron donor moiety and the electron acceptor moiety are combined to first and eighth positions of the naphthalene core with a benzene linker, respectively.

In another aspect of the embodiment of the invention provided is an organic light emitting diode including a first electrode; a second electrode facing the first electrode; and an organic emitting layer between the first and second electrodes and including a space-through charge transfer compound of

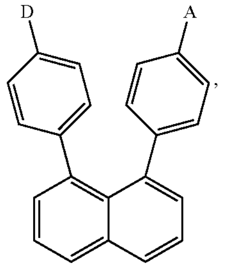

wherein D is selected from

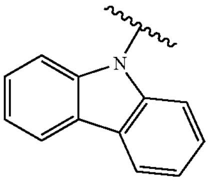
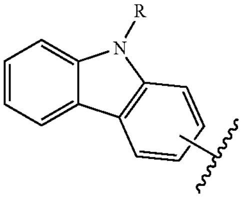
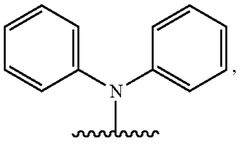

and A is selected from

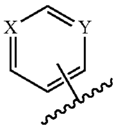
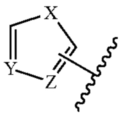
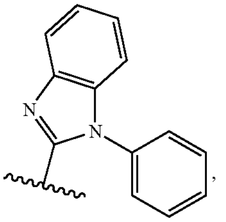

wherein R is selected from hydrogen, C1~C8 alkyl and C6~C20 aryl, and wherein X, Y, Z are independently selected from carbon and nitrogen, and at least one selected from X and Y is nitrogen.

In another aspect of the embodiment of the invention provided is a display device including a substrate; an organic light emitting diode on the substrate and including a first electrode, a second electrode facing the first electrode and an organic emitting layer between the first and second electrodes and including a space-through charge transfer compound; an encapsulation film on the organic light emitting diode; and a cover window on the encapsulation film, wherein the space-through charge transfer compound includes a naphthalene core, an electron donor moiety selected from carbazole and phenylcarbazole, and an electron acceptor moiety selected from pyridine, diazine, triazole, and phenyl benzodiazole, and wherein the electron donor moiety and the electron acceptor moiety are combined to first and eighth positions of the naphthalene core with a benzene linker, respectively.

In another aspect of the embodiment of the invention provided is a display device including a substrate; an organic light emitting diode on the substrate and including a first electrode, a second electrode facing the first electrode and an organic emitting layer between the first and second electrodes and including a space-through charge transfer compound of Formula 1; an encapsulation film on the organic light emitting diode; and a cover window on the encapsulation film,

[Formula 1]

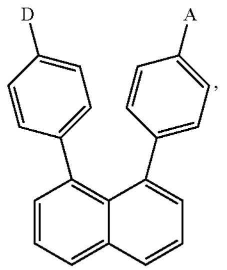

wherein D is selected from

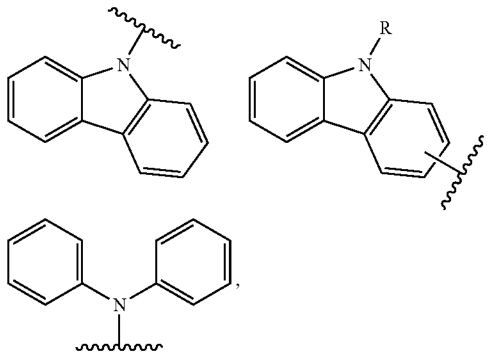

and A is selected from

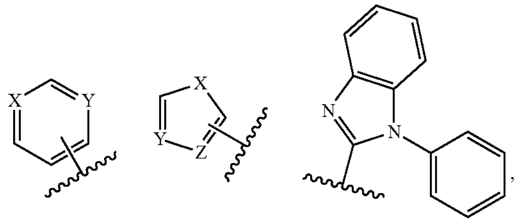

wherein R is selected from hydrogen, C1~C8 alkyl and C6~C20 aryl, and wherein X, Y, Z are independently selected from carbon and nitrogen, and at least one selected from X and Y is nitrogen.

It is to be understood that both the foregoing general description and the following detailed description are by example and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE EMBODIMENTS

Figure 1:
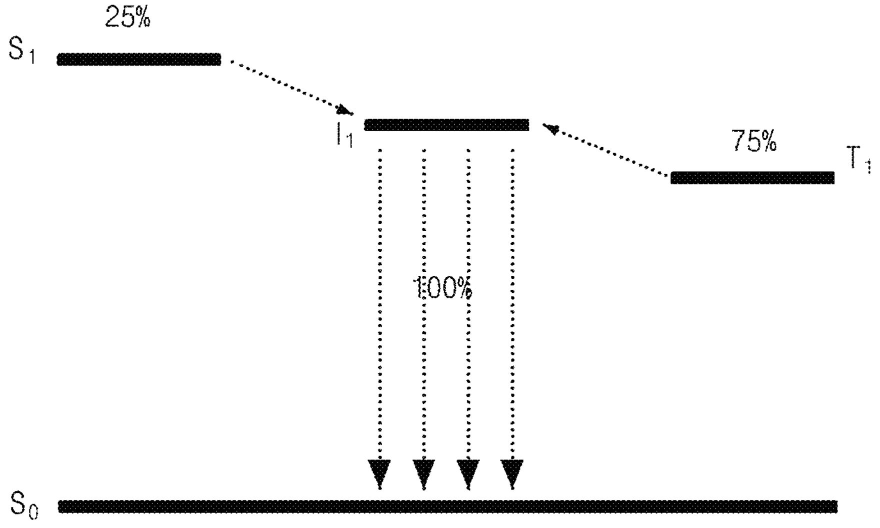
FIG. 1 is a view illustrating an emission mechanism of a space-through charge transfer compound, according to the present invention.
Figure 2A:
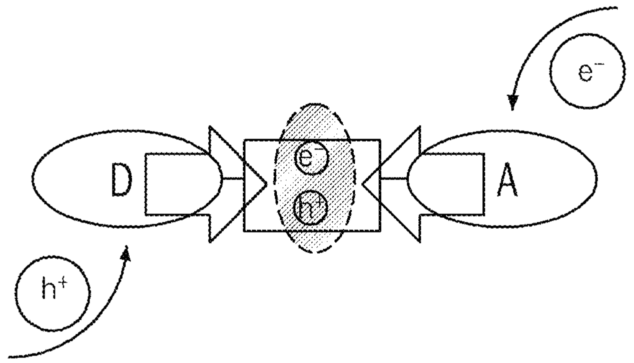
FIGS. 2A and 2B are views illustrating charge transfer in a space-through charge transfer compound, according to the present invention.
Figure 2B:
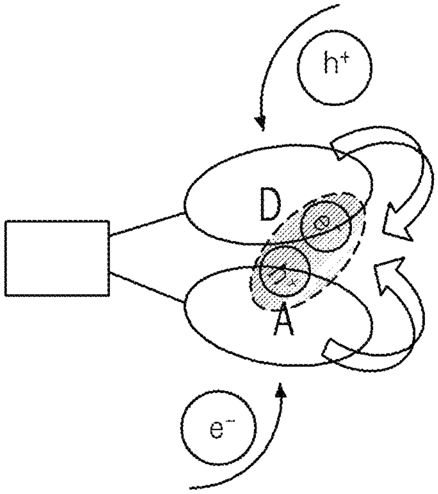

The meanings of terms described in the present specification should be understood as follows.

The singular forms should be understood as including the plural forms as well unless the context clearly indicates otherwise. The terms "first", "second", and the like are used to discriminate any one element from other elements and the scope of the present invention is not intended to be limited by these terms. The terms "comprises" "includes" and the like should be understood as not precluding the presence or addition of one or more other features, integers, steps, operations, elements, components, or combinations thereof. The term "at least one" should be understood as including all combinations that may be suggested from one or more associated items. For example, the meanings of "at least one selected from a first item, a second item, and a third item" includes not only each of the first item, the second item, and the third item, but also all combinations of these items that may be suggested from two or more ones of the first item, the second item, and the third item. In addition, when any one element is referred to as being "on" another element, it can be directly on the upper surface of the other element or a third intervening element may also be present.

Reference will now be made in detail to example embodiments, examples of which are illustrated in the accompanying drawings.

A space-through charge transfer compound of the present invention has a structure in that an electron donor moiety and an electron acceptor moiety are combined to first and eighth positions of a naphthalene core with a benzene linker and has Formula 1 of following.

[Formula 1]

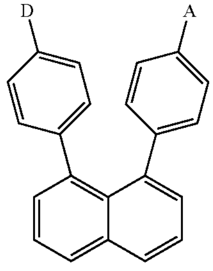

In the Formula 1, the electron donor moiety "D" is selected from formula 2.

[Formula 2]

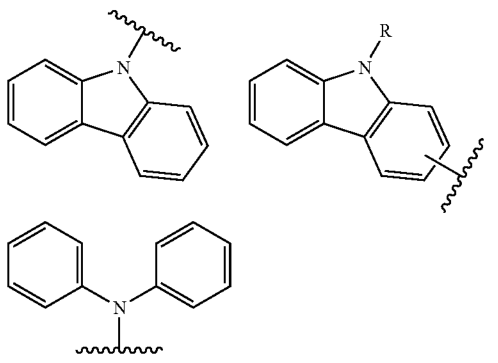

In the Formula 2, R is hydrogen, C1~C8 alkyl, or C6~C20 aryl.

For example, the electron donor moiety "D" may be selected from carbazole, phenylcarbazole, and biphenylamine.

In the Formula 1, the electron acceptor moiety "A" is selected from Formula 3.

[Formula 3]

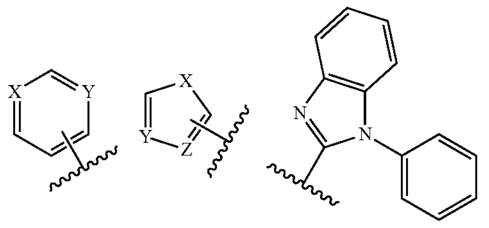

In the formula 3, X, Y, and Z are independently selected from carbon and nitrogen, and at least one selected from X and Y is nitrogen. X, Y and Z are same or different.

For example, the electron acceptor "A" may be selected from pyridine, diazine, triazole and phenyl benzodiazole.

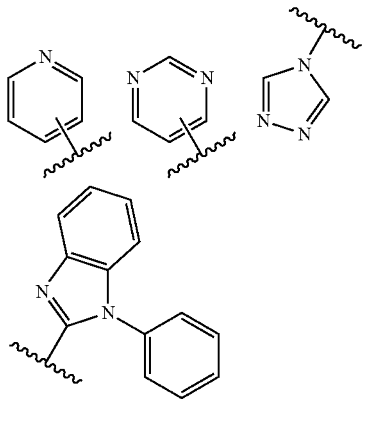

In the space-through charge transfer compound, the electron donor moiety and the electron acceptor moiety are combined or linked in the molecule such that an overlap between highest occupied molecular orbital (HOMO) and lowest unoccupied molecular orbital (LUMO) is reduced. As a result, a charge transfer complex is generated, and the emitting efficiency of the space-through charge transfer compound is improved. Namely, in the space-through charge transfer compound, the triplet exciton is used for emission such that the emitting efficiency is improved.

In other words, since the space-through charge transfer compound of the present invention includes both of the electron donor moiety and the electron acceptor moiety, the charge is easily transferred in the molecule, and the emission efficiency is improved.

In the space-through charge transfer compound of the present invention, since the electron donor moiety and the electron acceptor moiety are combined or linked to the first and eighth positions of the naphthalene core, a gap or a distance between the electron donor moiety and the electron acceptor moiety is decreased or minimized. Accordingly, the charge transfer is directly generated through a space between the electron donor moiety and the electron acceptor moiety such that the conjugation length in the space-through charge transfer compound becomes shorter than another compound where the charge transfer is generated through a bonding orbital. As a result, a red shift problem in the emitted light can be prevented, and the space-through charge transfer compound of the present invention can provide deep blue emission.

In addition, the space-through charge transfer compound of the present invention includes the benzene linker being capable of minimizing the steric hinderance between the electron donor moiety and the electron acceptor moiety such that the stability of the compound is increased.

Referring to FIG. 1, which is a view illustrating an emission mechanism of a space-through charge transfer compound according to the present invention, in the space-through charge transfer compound of the present invention, the triplet excitons as well as the singlet excitons are engaged in the emission such that the emitting efficiency is improved.

Namely, the triplet exciton is activated by a field, and the triplet exciton and the singlet exciton are transferred into an intermediated state "$I_1$" and transited into a ground state "So" to emit the light. In other words, the singlet state "$S_1$" and the triplet state "$T_1$" are transited into the intermediated state "$I_1$" ($S_1 \rightarrow I_1 \leftarrow T_1$), and the singlet exciton and the triplet exciton in the intermediated state "$I_1$" are engaged in the emission such that the emitting efficiency is improved. The compound having the above emission mechanism may be referred to as a field activated delayed fluorescence (FADF) compound.

In the related art fluorescence compound, since the HOMO and the LUMO are dispersed throughout an entirety of the molecule, the interconversion of the HOMO and the LUMO is impossible. (Selection Rule.)

However, in the FADF compound, since the overlap between the HOMO and the LUMO in the molecule is relatively small, the interaction between the HOMO and the LUMO is small. Accordingly, changes of the spin state of one electron do not affect other electrons, and a new charge transfer band, which does not comply with the Selection Rule, is generated.

Moreover, since the electron donor moiety and the electron acceptor moiety is spatially spaced apart from each other in the molecule, the dipole moment is generated in a polarized state. In the polarized state dipole moment, the interaction between the HOMO and the LUMO is further reduced such that the emission mechanism does not comply with the Selection Rule. Accordingly, in the FADF compound, the transition from the triplet state "$T_1$" and the singlet state "$S_1$" into the intermediated state "$I_1$" can be generated such that the triplet exciton can be engaged in the emission.

When the OLED is driven, the intersystem transition (intersystem crossing) from 25% singlet state "$S_1$" excitons and 75% triplet state "$T_1$" excitons to the intermediated state "$I_1$" is generated, and the singlet and triplet excitons in the intermediated state "$I_1$" are transited into the ground state to emit the light. As a result, the FADF compound has the theoretic quantum efficiency of 100%.

For example, the space-through charge transfer compound in the Formula 1 may be one of compounds in Formula 4.

[Formula 4]

1

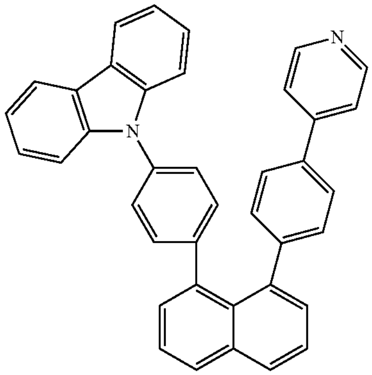

2

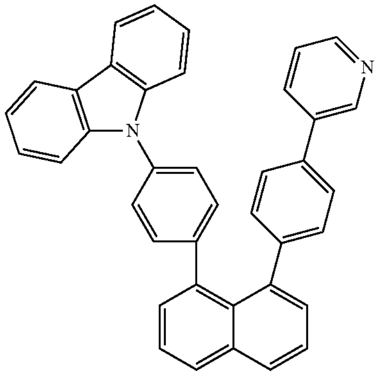

3

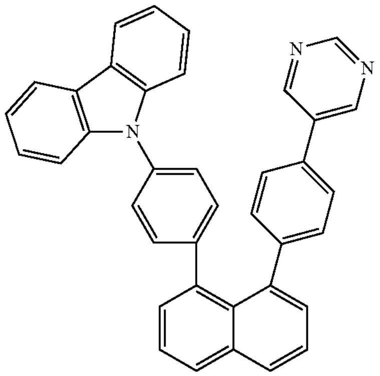

-continued

4

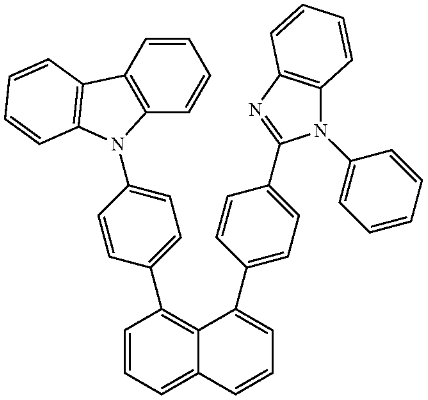

5

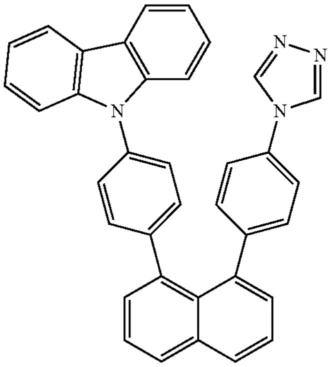

6

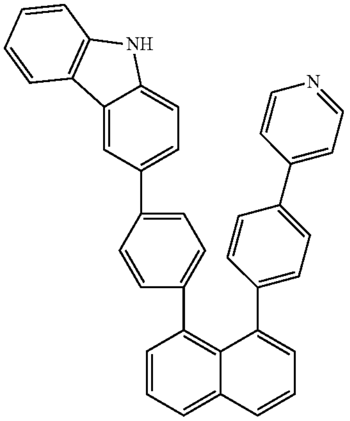

7

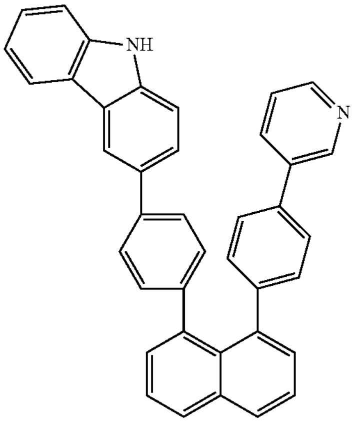

-continued
8
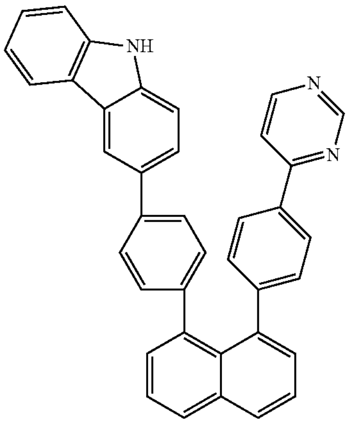
9
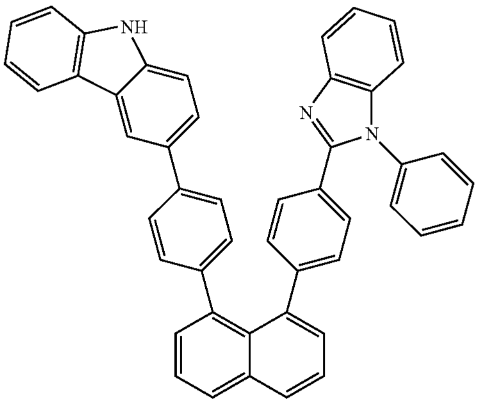
10
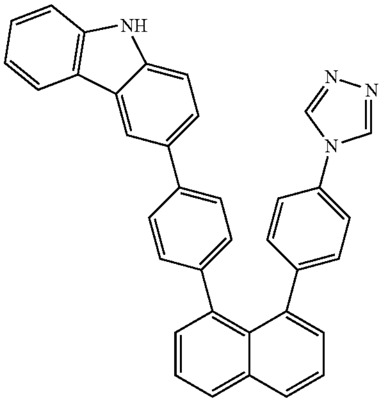
11
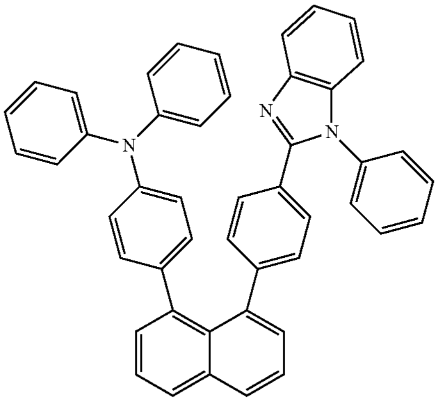
-continued
12
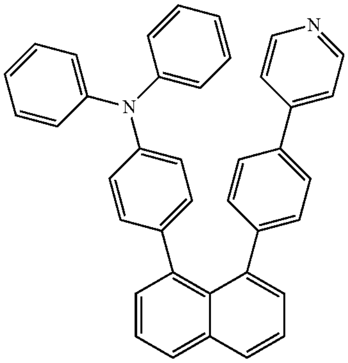
13
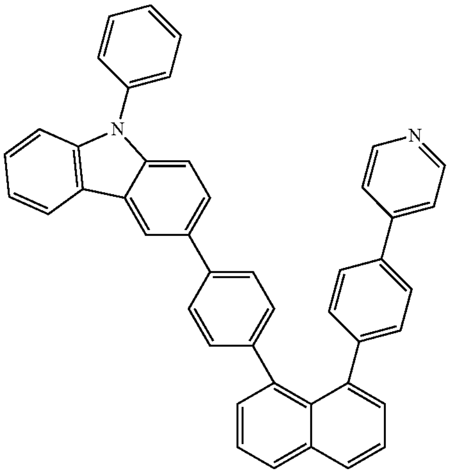
14
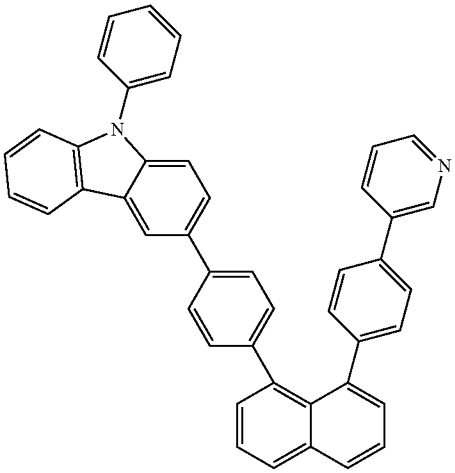

-continued

15

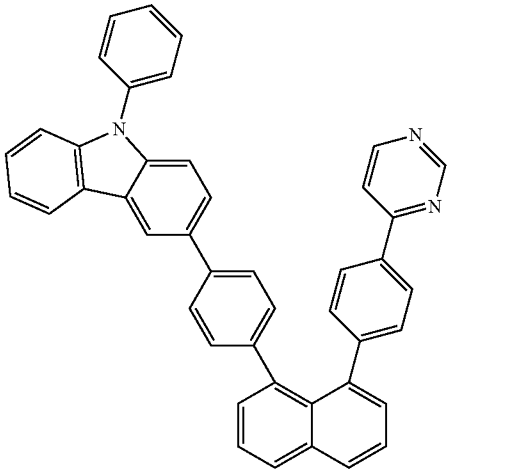

16

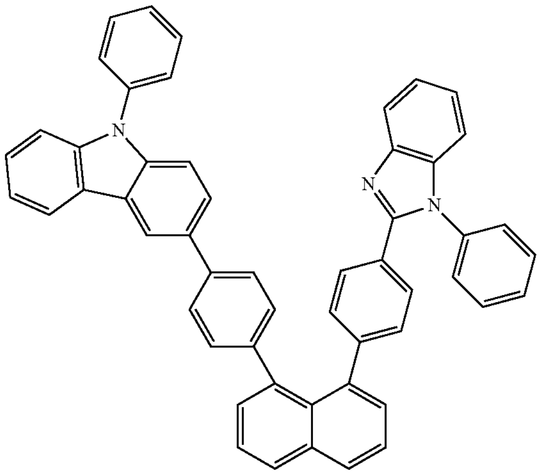

17

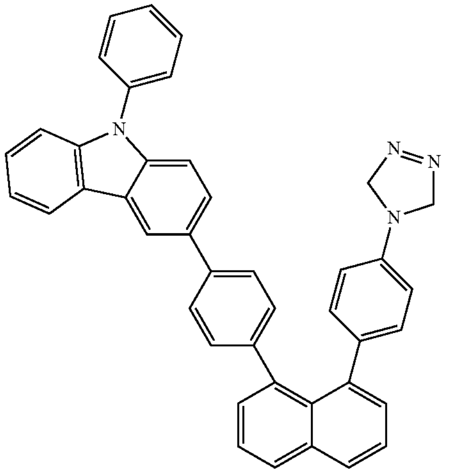

The space-through charge transfer compound of the present invention has a wide energy band gap such that the emission efficiency of the OLED using the compound is improved.

The HOMO, the LUMO and the energy band gap of the compounds 1 to 12 are listed in Table 1.

TABLE 1

| | HOMO (eV) | LUMO (eV) | Band gap |
|---|---|---|---|
| compound 1 | −5.53 | −1.57 | 3.96 |
| compound 2 | −5.54 | −1.64 | 3.90 |
| compound 3 | −5.57 | −1.72 | 3.85 |
| compound 4 | −5.55 | −1.69 | 3.86 |
| compound 5 | −5.54 | −1.77 | 3.77 |
| compound 6 | −5.89 | −1.55 | 4.34 |
| compound 7 | −5.86 | −1.62 | 4.24 |
| compound 8 | −5.87 | −1.70 | 4.17 |
| compound 9 | −5.86 | −1.65 | 4.21 |
| compound 10 | −5.86 | −1.81 | 4.05 |
| compound 11 | −5.17 | −1.70 | 3.47 |
| compound 12 | −5.18 | −1.59 | 3.59 |

Synthesis

1. Synthesis of Compound 1

(1) Compound C

[Reaction Formula 1-1]

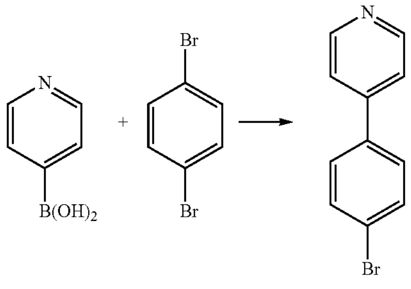

A B C

In the $N_2$ gas purging system, compound A, compound B of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methyl chloride (2:1) such that compound C of white solid was obtained.

(2) Compound D

[Reaction Formula 1-2]

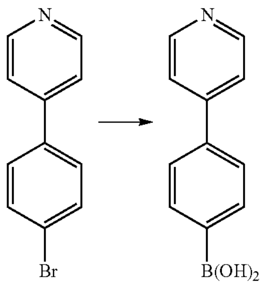

C D

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised into the room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound G

[Reaction Formula 1-3]

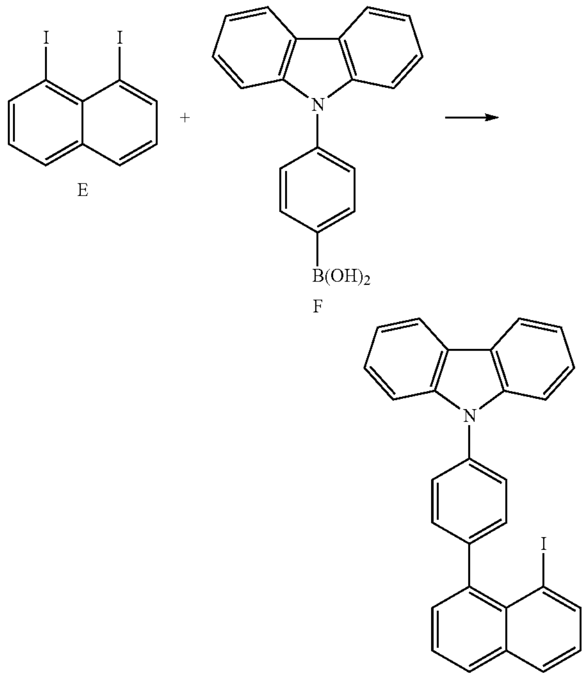

E F G

In the $N_2$ gas purging system, compound E, compound F of 0.9 equivalent, Pd(0) of 0.05 equivalent and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane such that compound G of white solid was obtained.

(4) Compound 1

[Reaction Formula 1-4]

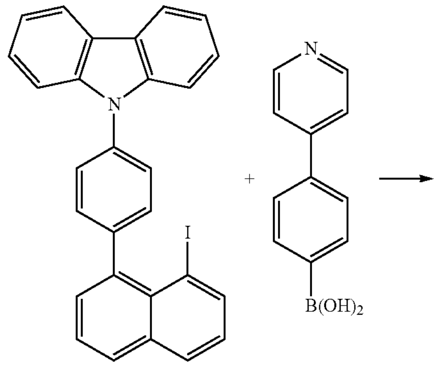

G D

-continued

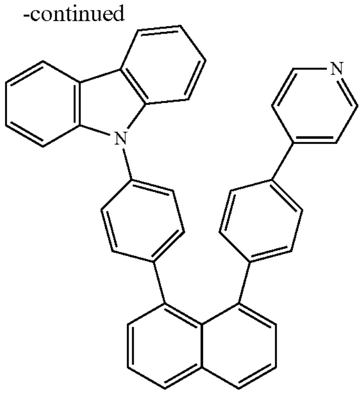

In the $N_2$ gas purging system, compound G, compound D of 1.2 equivalent, Pd(0) of 0.05 equivalent and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and ethylene acetate (8:2) such that the compound 1 of white solid was obtained.

2. Synthesis of Compound 2

(1) Compound C

[Reaction Formula 2-1]

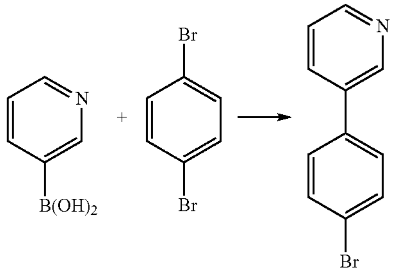

A B C

In the $N_2$ gas purging system, compound A, compound B of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methyl chloride (2:1) such that compound C of white solid was obtained.

(2) Compound D

[Reaction Formula 2-2]

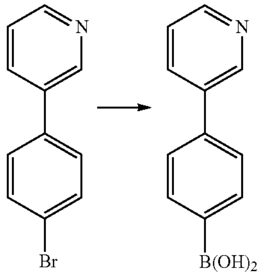

C D

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound G

[Reaction Formula 2-3]

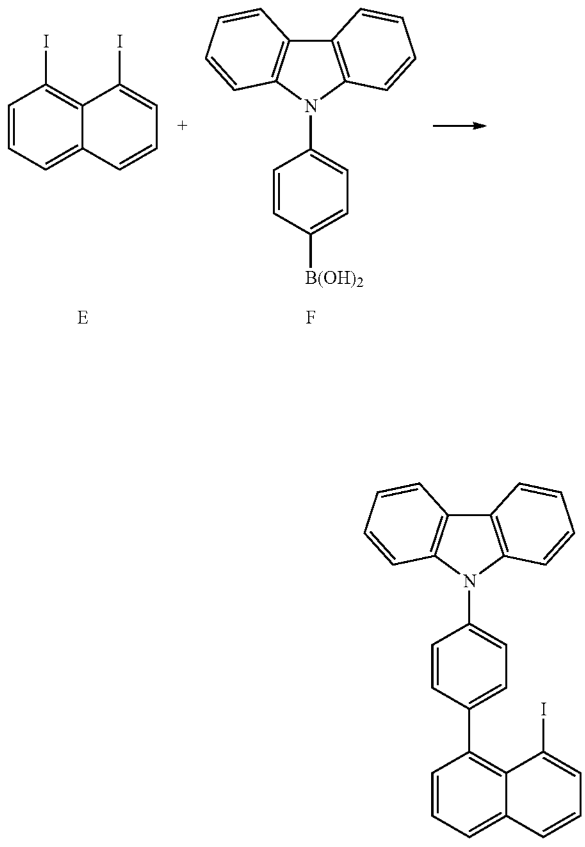

E F

G

In the $N_2$ gas purging system, compound E, compound F of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane such that compound G of white solid was obtained.

(4) Compound 2

[Reaction Formula 2-4]

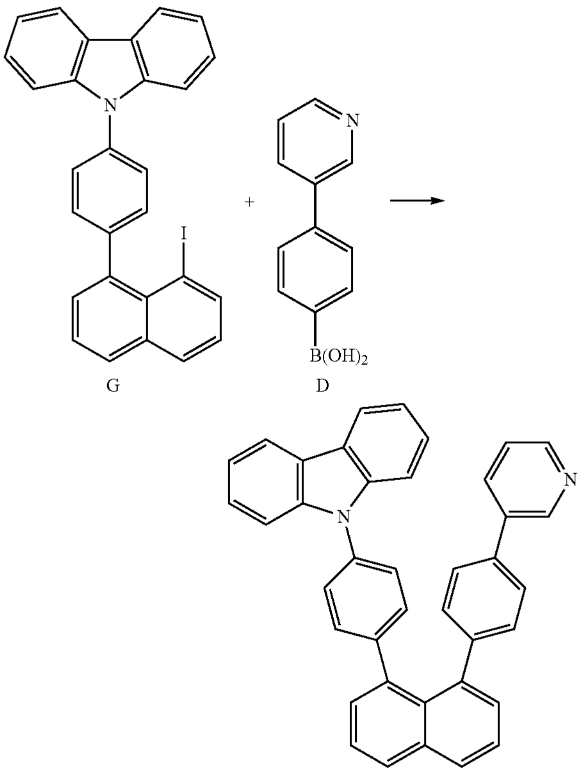

G D

In the $N_2$ gas purging system, compound G, compound D of 1.2 equivalent, Pd(0) of 0.05 equivalent and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and ethylene acetate (8:2) such that the compound 2 of white solid was obtained.

3. Synthesis of Compound 3

(1) Compound C

[Reaction Formula 3-1]

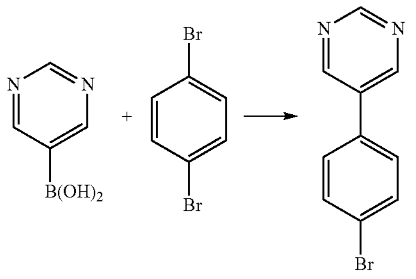

A B C

In the $N_2$ gas purging system, compound A, compound B of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methyl chloride (2:1) such that compound C of white solid was obtained.

(2) Compound D

[Reaction Formula 3-2]

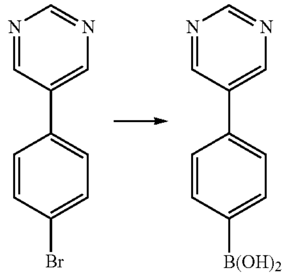

C D

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound G

[Reaction Formula 3-3]

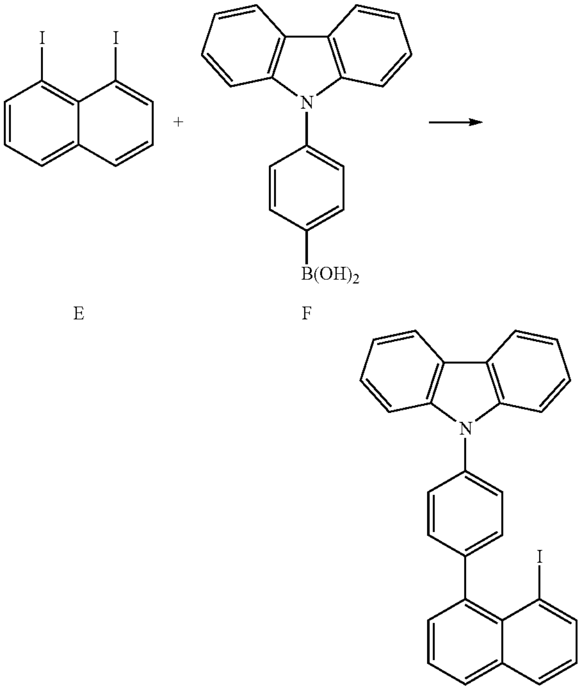

E F

G

In the $N_2$ gas purging system, compound E, compound F of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane such that compound G of white solid was obtained.

(4) Compound 3

[Reaction Formula 3-4]

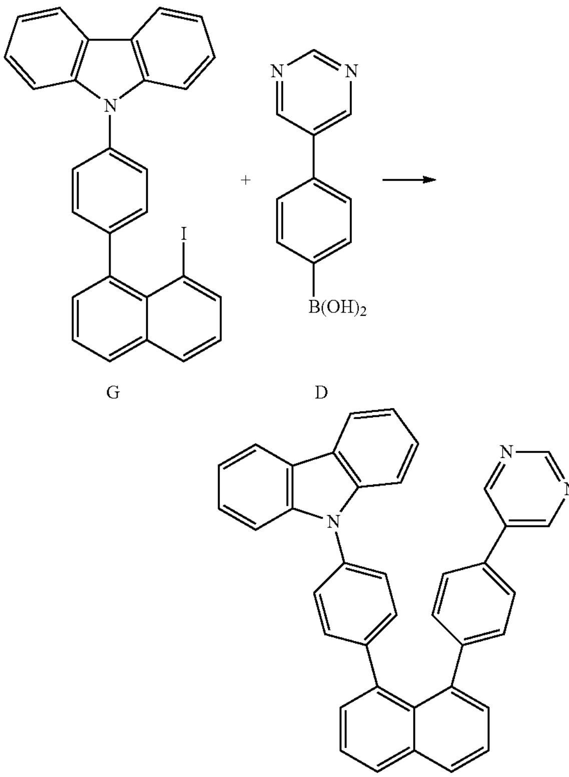

G D

In the $N_2$ gas purging system, compound G, compound D of 1.2 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and ethylene acetate (9:1) such that the compound 3 of white solid was obtained.

4. Synthesis of Compound 4

(1) Compound C

[Reaction Formula 4-1]

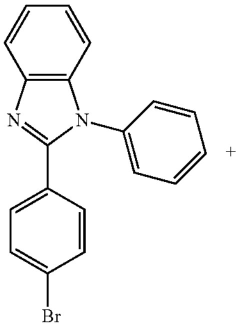

A

-continued

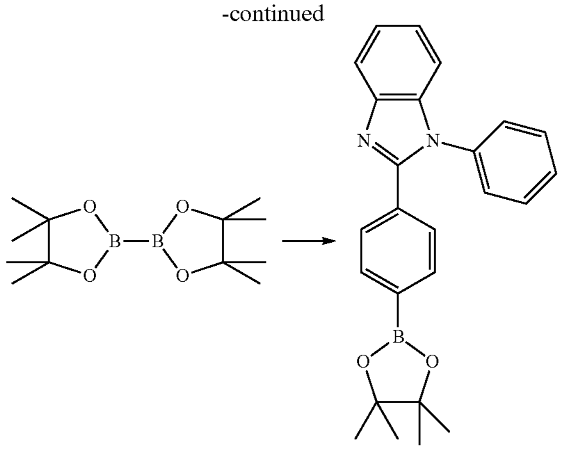

B C

In the $N_2$ gas purging system, compound A, Bu—Li of 1.5 equivalent were put into ether, and the mixture was stirred under a temperature of −78° C. After completion of the reaction for 2 hours, compound B of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound C was obtained.

(2) Compound F

[Reaction Formula 4-2]

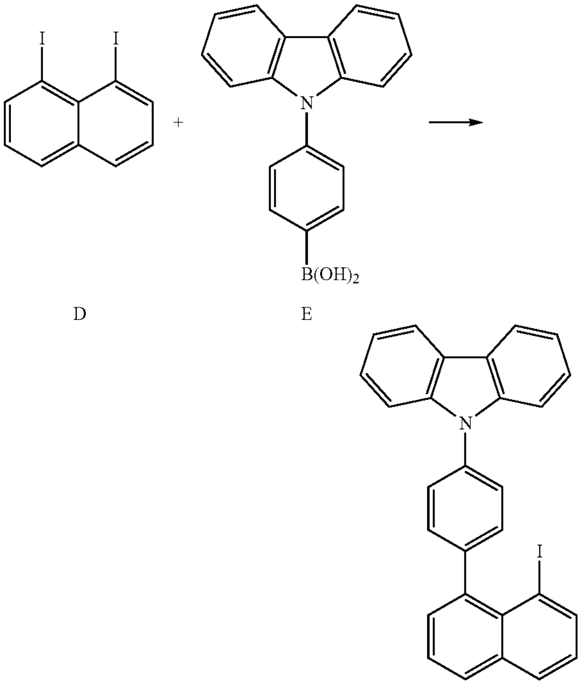

D E F

In the $N_2$ gas purging system, compound D, compound E of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane such that compound F of white solid was obtained.

(3) Compound 4

[Reaction Formula 4-3]

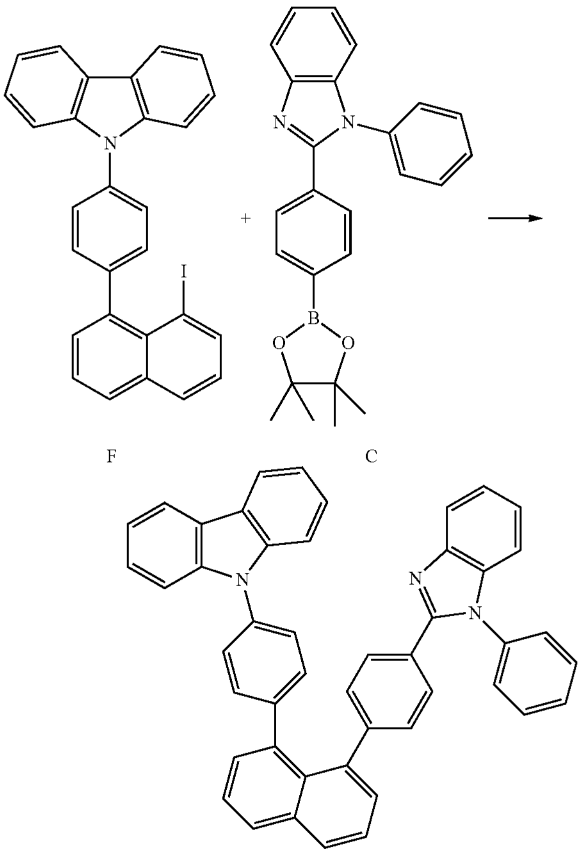

In the $N_2$ gas purging system, compound F, compound C of 1.2 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and ethylene acetate (6:4) such that the compound 4 of white solid was obtained.

5. Synthesis of Compound 5

(1) Compound C

[Reaction Formula 5-1]

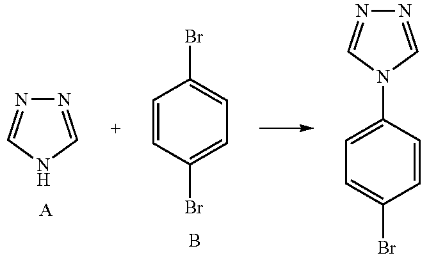

A B C

In the N2 gas purging system, compound A, compound B of 0.9 equivalent, Pd(0) of 0.05 equivalent and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane such that compound C of white solid was obtained.

(2) Compound D

[Reaction Formula 5-2]

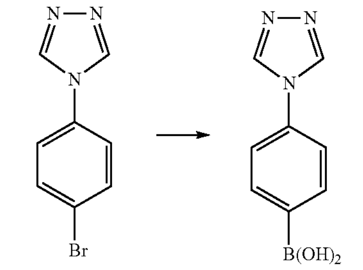

C D

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound G

[Reaction Formula 5-3]

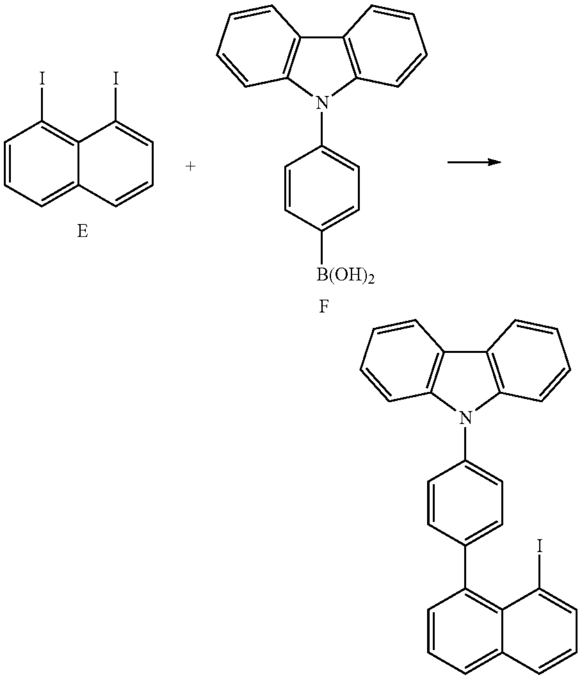

E F G

In the $N_2$ gas purging system, compound E, compound F of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane such that compound G of white solid was obtained.

(4) Compound 5

[Reaction Formula 5-4]

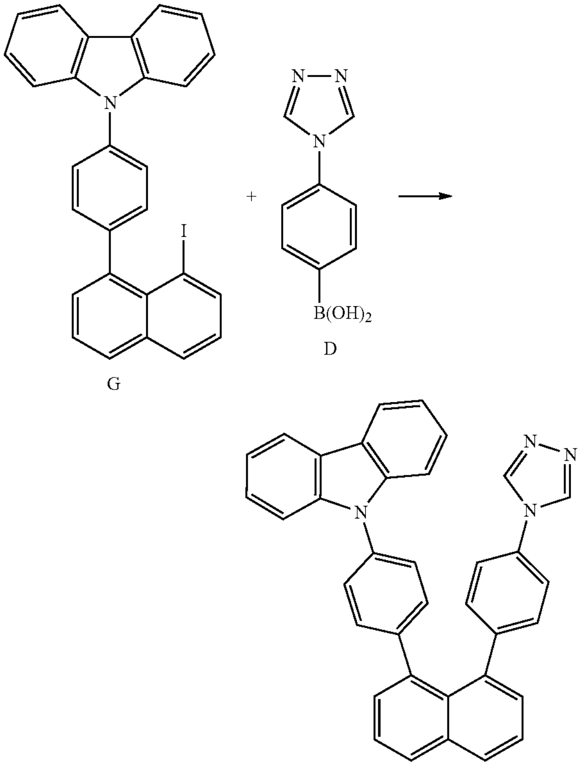

G D

In the $N_2$ gas purging system, compound G, compound D of 1.2 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methylene chloride (7:3) such that the compound 5 of white solid was obtained.

6. Synthesis of Compound 6

(1) Compound C

[Reaction Formula 6-1]

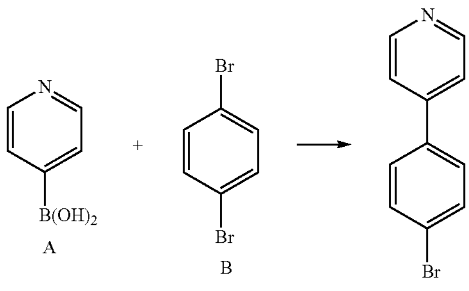

A B C

In the $N_2$ gas purging system, compound A, compound B of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methyl chloride (2:1) such that compound C of white solid was obtained.

(2) Compound D

[Reaction Formula 6-2]

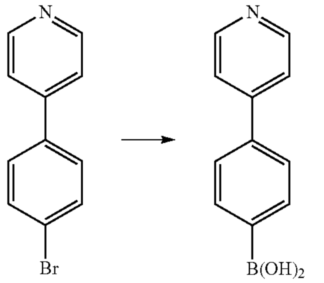

C D

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound G

[Reaction Formula 6-3]

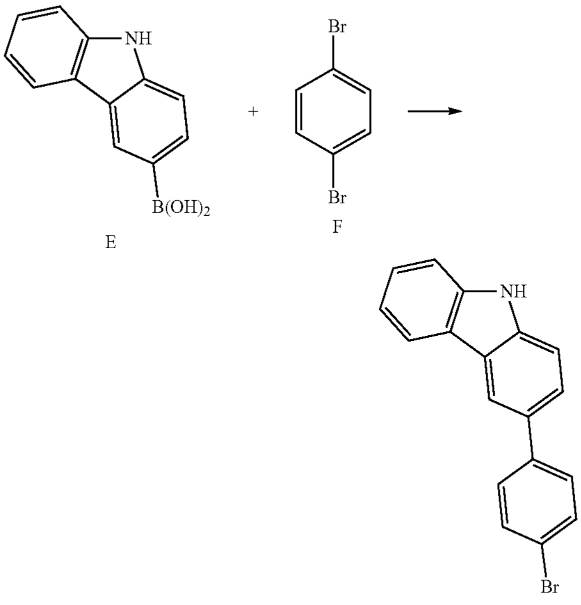

E F G

In the $N_2$ gas purging system, compound E, compound F of 0.9 equivalent, Pd(0) of 0.05 equivalent, and potassium carbonate of 4.0 equivalent were put into toluene, and the mixture was stirred in an oil bath under a temperature of 80° C. 12 hours after, water was added into the mixture to be extracted, and the resultant was columned using the developing solvent of hexane such that compound G of white solid was obtained.

(4) Compound H

[Reaction Formula 6-4]

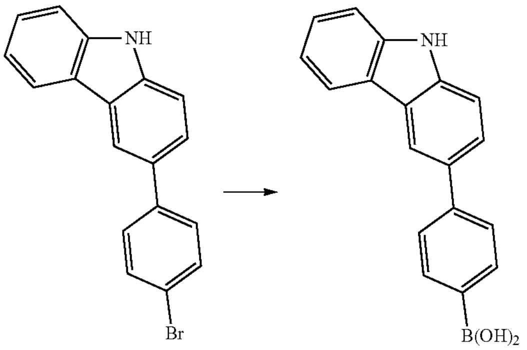

G H

In the $N_2$ gas purging system, compound G, Bu—Li of 1.5 equivalent were put into ether, and the mixture was stirred under a temperature of −78° C. After completion of the reaction for 4 hours, triethyl borate of 1.2 equivalent was added, and the mixture was stirred for 30 minutes under a temperature of −78° C. The reaction temperature was raised in room temperature by removing a dry-ice bath. After completion of the reaction for 16 hours, HCl (30 ml) diluted by DI water was added to remove the organic solvent. After completely removing the organic solvent, the white solid, which is precipitated in water, was filtered such that compound H was obtained.

(5) Compound J

[Reaction Formula 6-5]

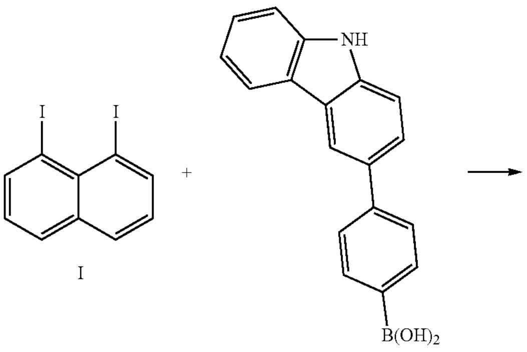

I H

-continued

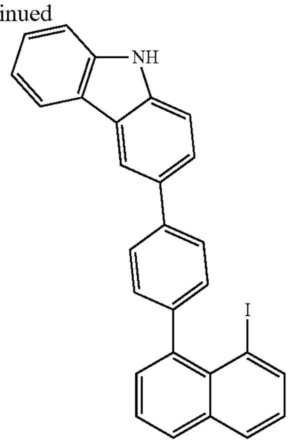

J

In the $N_2$ gas purging system, compound I, compound H of 0.9 equivalent, Pd(0) of 0.05 equivalent and potassium carbonate of 4.0 equivalent were put into toluene, and the mixture was stirred in an oil bath under a temperature of 80° C. 8 hours after, water was added into the mixture to be extracted, and the resultant was columned using the developing solvent of hexane such that compound J of white solid was obtained.

(6) Compound 6

[Reaction Formula 6-6]

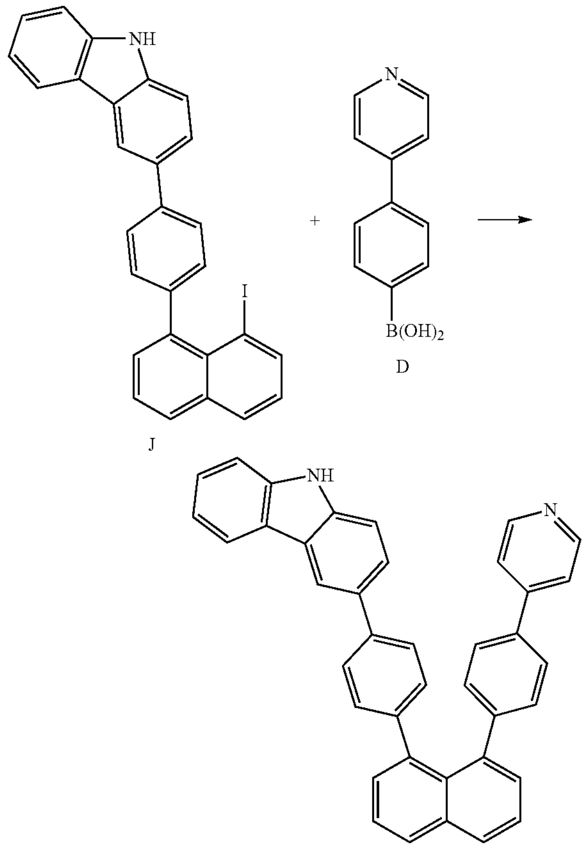

J D

In the $N_2$ gas purging system, compound J, compound D of 1.2 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and ethylene acetate (8:2) such that the compound 6 of white solid was obtained.

7. Synthesis of Compound 7

(1) Compound C

[Reaction Formula 7-1]

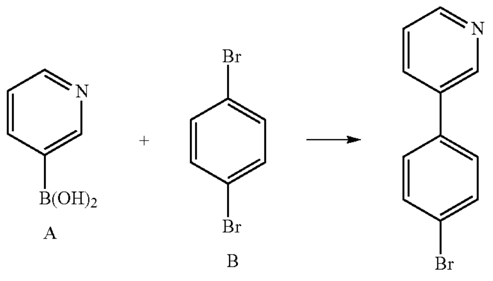

A B C

In the $N_2$ gas purging system, compound A, compound B of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methyl chloride (2:1) such that compound C of white solid was obtained.

(2) Compound D

[Reaction Formula 7-2]

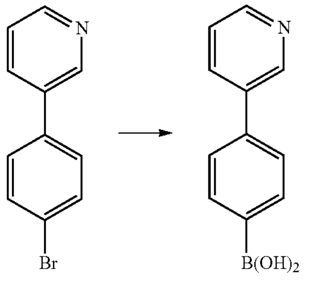

C D

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound G

[Reaction Formula 7-3]

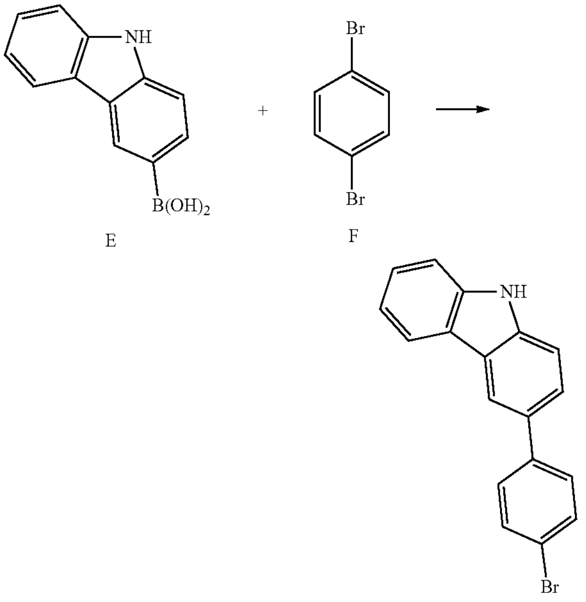

E F G

In the $N_2$ gas purging system, compound E, compound F of 0.9 equivalent, Pd(0) of 0.05 equivalent, and potassium carbonate of 4.0 equivalent were put into toluene, and the mixture was stirred in an oil bath under a temperature of 80° C. 12 hours after, water was added into the mixture to be extracted, and the resultant was columned using the developing solvent of hexane such that compound G of white solid was obtained.

(4) Compound H

[Reaction Formula 7-4]

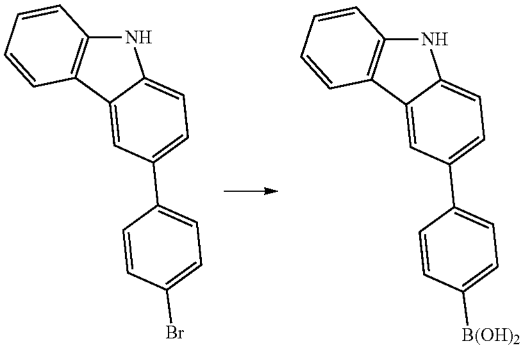

G H

In the $N_2$ gas purging system, compound G, Bu—Li of 1.5 equivalent were put into ether, and the mixture was stirred under a temperature of −78° C. After completion of the reaction for 4 hours, triethyl borate of 1.2 equivalent was added, and the mixture was stirred for 30 minutes under a temperature of −78° C. The reaction temperature was raised in room temperature by removing a dry-ice bath. After completion of the reaction for 16 hours, HCl (30 ml) diluted by DI water was added to remove the organic solvent. After completely removing the organic solvent, the white solid, which is precipitated in water, was filtered such that compound H was obtained.

(5) Compound J

[Reaction Formula 7-5]

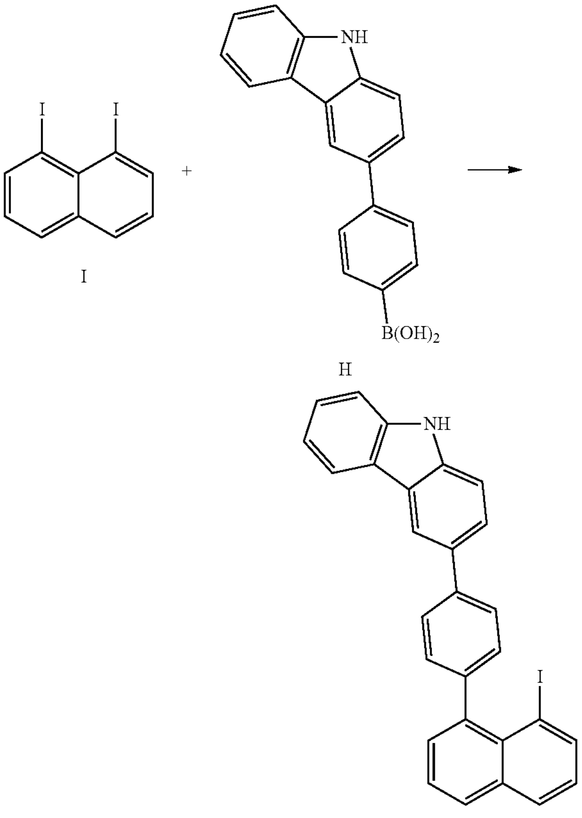

I H J

In the $N_2$ gas purging system, compound I, compound H of 0.9 equivalent, Pd(0) of 0.05 equivalent, and potassium carbonate of 4.0 equivalent were put into toluene, and the mixture was stirred in an oil bath under a temperature of 80° C. 8 hours after, water was added into the mixture to be extracted, and the resultant was columned using the developing solvent of hexane such that compound J of white solid was obtained.

(6) Compound 7

[Reaction Formula 7-6]

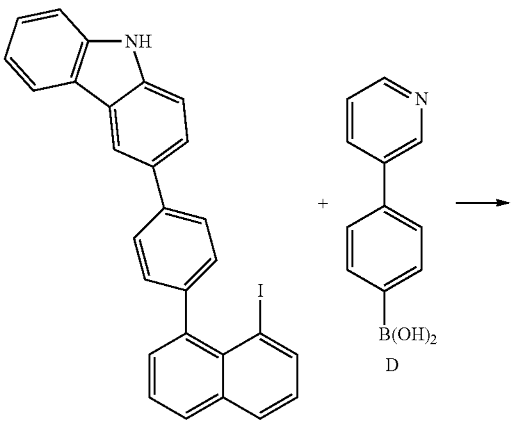

J D

-continued

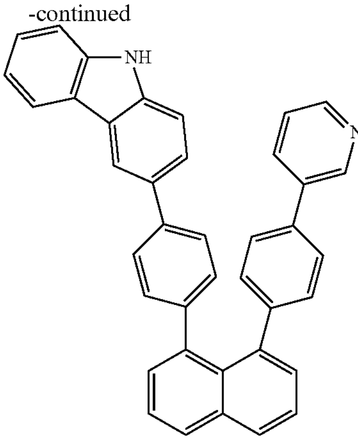

In the $N_2$ gas purging system, compound J, compound D of 1.2 equivalent, Pd(0) of 0.05 equivalent and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and ethylene acetate (8:2) such that the compound 7 of white solid was obtained.

8. Synthesis of Compound 8

(1) Compound C

[Reaction Formula 8-1]

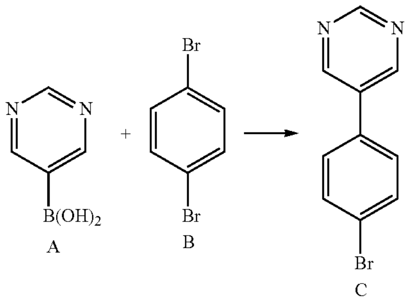

In the $N_2$ gas purging system, compound A, compound B of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methyl chloride (2:1) such that compound C of white solid was obtained.

(2) Compound D

[Reaction Formula 8-2]

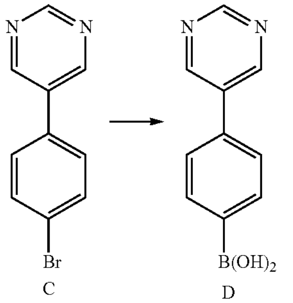

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound G

[Reaction Formula 8-3]

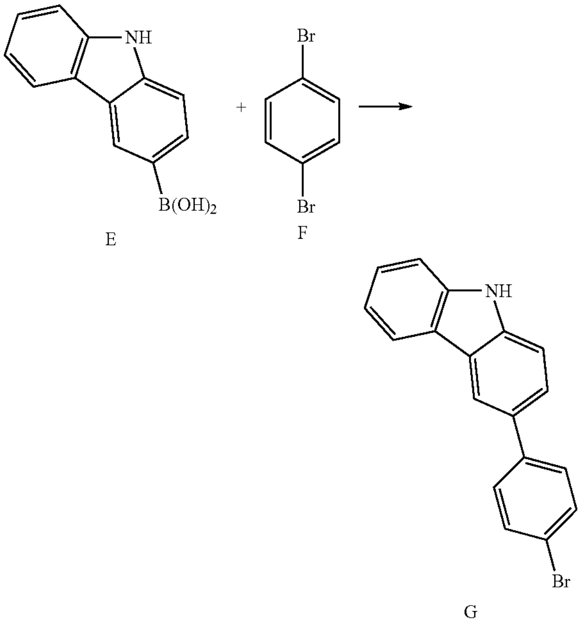

In the $N_2$ gas purging system, compound E, compound F of 0.9 equivalent, Pd(0) of 0.05 equivalent, and potassium carbonate of 4.0 equivalent were put into toluene, and the mixture was stirred in an oil bath under a temperature of 80° C. 12 hours after, water was added into the mixture to be extracted, and the resultant was columned using the developing solvent of hexane such that compound G of white solid was obtained.

(4) Compound H

[Reaction Formula 8-4]

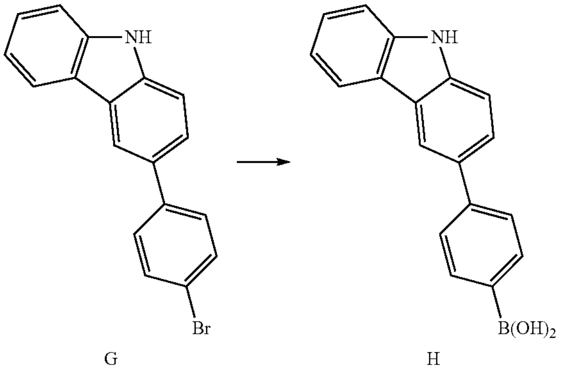

In the $N_2$ gas purging system, compound G, Bu—Li of 1.5 equivalent were put into ether, and the mixture was stirred under a temperature of −78° C. After completion of the reaction for 4 hours, triethyl borate of 1.2 equivalent was added, and the mixture was stirred for 30 minutes under a temperature of −78° C. The reaction temperature was raised in room temperature by removing a dry-ice bath. After completion of the reaction for 16 hours, HCl (30 ml) diluted by DI water was added to remove the organic solvent. After completely removing the organic solvent, the white solid, which is precipitated in water, was filtered such that compound H was obtained.

(5) Compound J

[Reaction Formula 8-5]

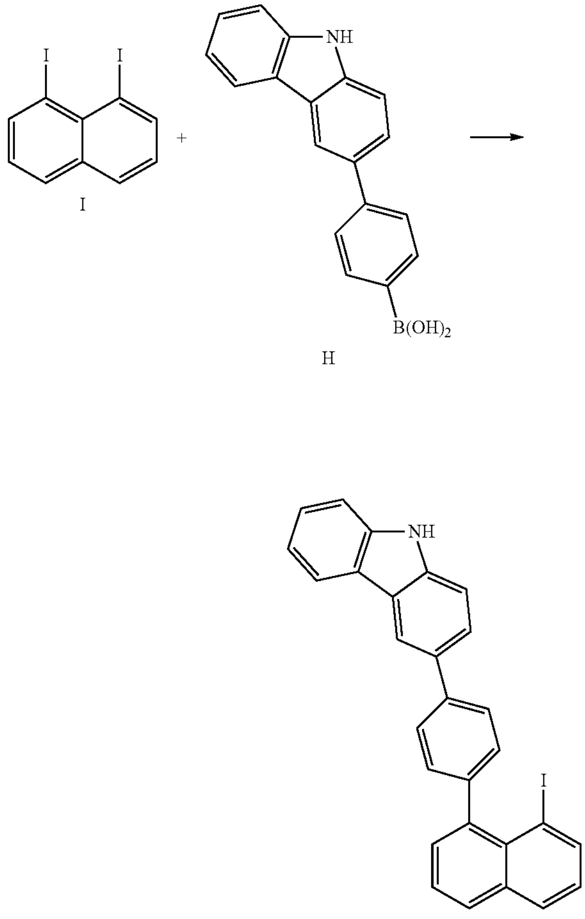

I

H

J

In the $N_2$ gas purging system, compound I, compound H of 0.9 equivalent, Pd(0) of 0.05 equivalent, and potassium carbonate of 4.0 equivalent were put into toluene, and the mixture was stirred in an oil bath under a temperature of 80° C. 8 hours after, water was added into the mixture to be extracted, and the resultant was columned using the developing solvent of hexane such that compound J of white solid was obtained.

(6) Compound 8

[Reaction Formula 8-6]

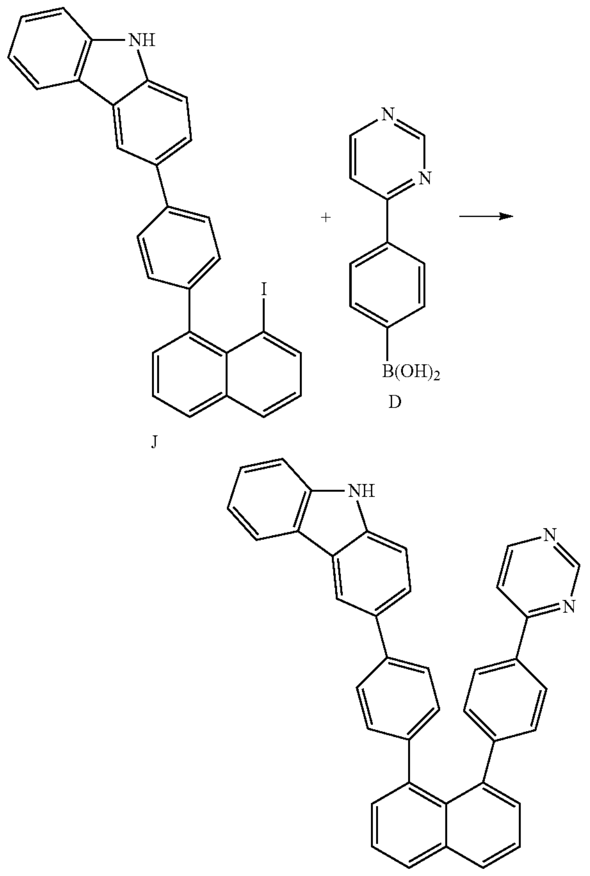

J

D

In the $N_2$ gas purging system, compound J, compound D of 1.2 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and ethylene acetate (9:1) such that the compound 8 of white solid was obtained.

9. Synthesis of Compound 9

(1) Compound C

[Reaction Formula 9-1]

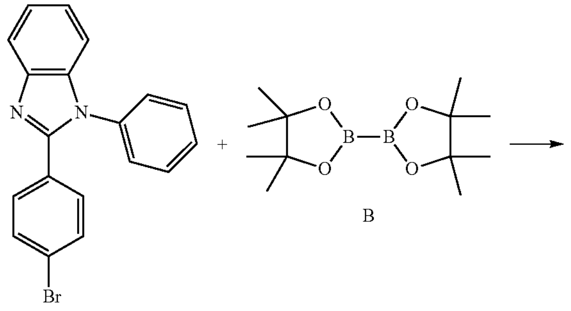

A

B

-continued

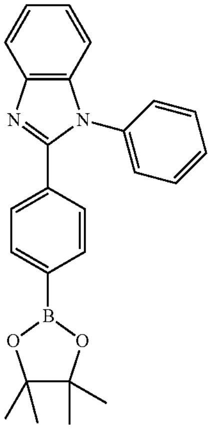

C

In the $N_2$ gas purging system, compound A, Bu—Li of 1.5 equivalent were put into ether, and the mixture was stirred under a temperature of −78° C. After completion of the reaction for 2 hours, compound B of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound C was obtained.

(2) Compound F

[Reaction Formula 9-2]

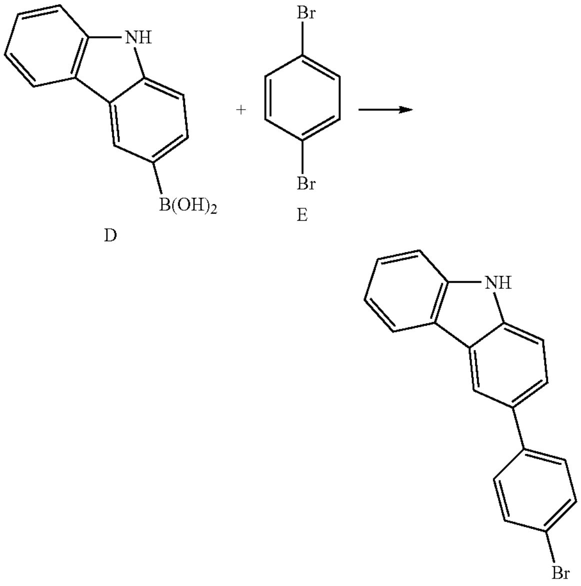

D E F

In the $N_2$ gas purging system, compound D, compound E of 0.9 equivalent, Pd(0) of 0.05 equivalent, and potassium carbonate of 4.0 equivalent were put into toluene, and the mixture was stirred in an oil bath under a temperature of 80° C. 12 hours after, water was added into the mixture to be extracted, and the resultant was columned using the developing solvent of hexane such that compound F of white solid was obtained.

(3) Compound G

[Reaction Formula 9-3]

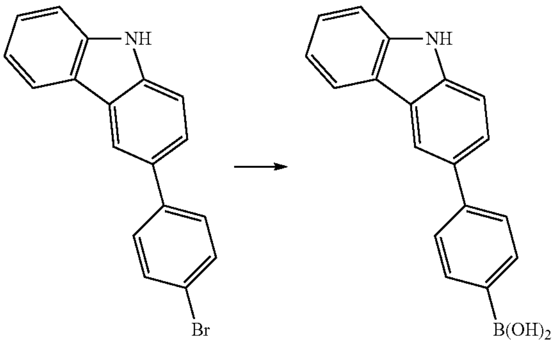

F G

In the $N_2$ gas purging system, compound F, Bu—Li of 1.5 equivalent were put into ether, and the mixture was stirred under a temperature of −78° C. After completion of the reaction for 4 hours, triethyl borate of 1.2 equivalent was added, and the mixture was stirred for 30 minutes under a temperature of −78° C. The reaction temperature was raised in room temperature by removing a dry-ice bath. After completion of the reaction for 16 hours, HCl (30 ml) diluted by DI water was added to remove the organic solvent. After completely removing the organic solvent, the white solid, which is precipitated in water, was filtered such that compound G was obtained.

(4) Compound I

[Reaction Formula 9-4]

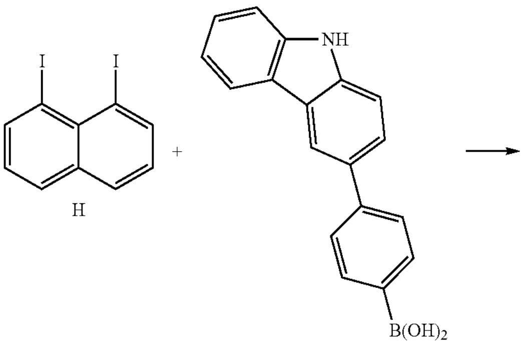

H G

-continued

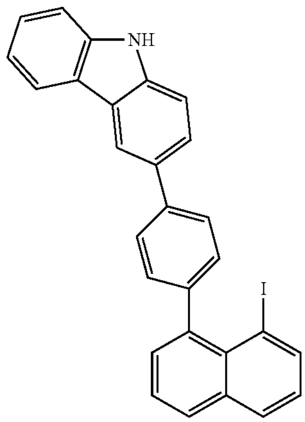

I

In the $N_2$ gas purging system, compound H, compound G of 0.9 equivalent, Pd(0) of 0.05 equivalent, and potassium carbonate of 4.0 equivalent were put into toluene, and the mixture was stirred in an oil bath under a temperature of 80° C. 8 hours after, water was added into the mixture to be extracted, and the resultant was columned using the developing solvent of hexane such that compound I of white solid was obtained.

(5) Compound 9

[Reaction Formula 9-5]

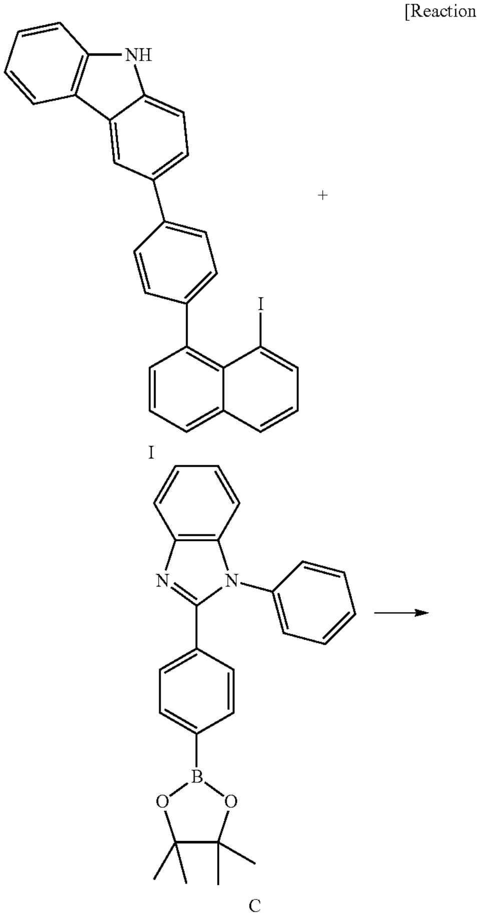

-continued

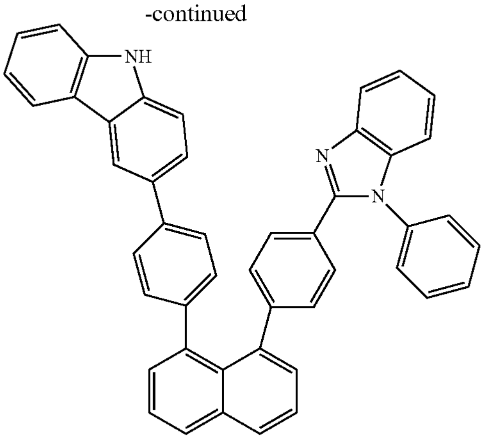

In the $N_2$ gas purging system, compound I, compound C of 1.2 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and ethylene acetate (9:1) such that the compound 9 of white solid was obtained.

10. Synthesis of Compound 10

(1) Compound C

[Reaction Formula 10-1]

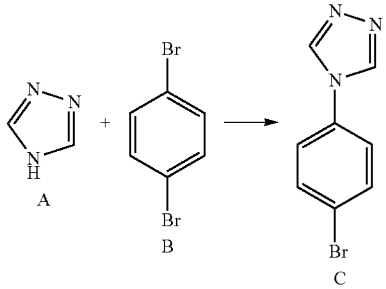

In the $N_2$ gas purging system, compound A, compound B of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane such that compound C of white solid was obtained.

(2) Compound D

[Reaction Formula 10-2]

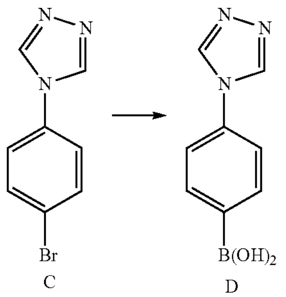

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound G

[Reaction Formula 10-3]

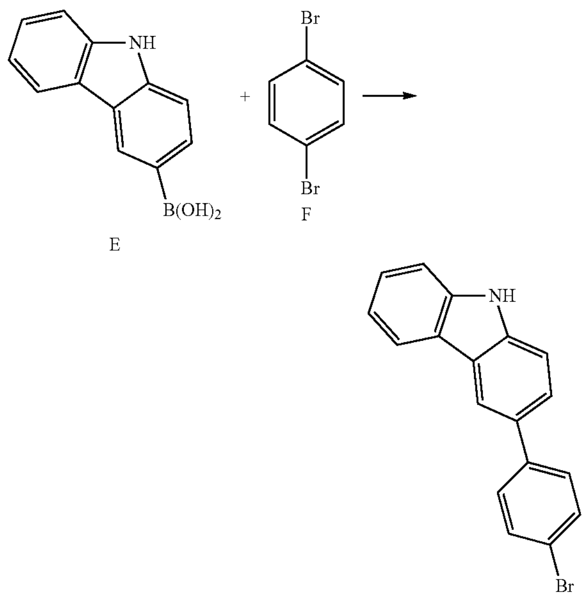

E F

G

In the $N_2$ gas purging system, compound E, compound F of 0.9 equivalent, Pd(0) of 0.05 equivalent, and potassium carbonate of 4.0 equivalent were put into toluene, and the mixture was stirred in an oil bath under a temperature of 80° C. 12 hours after, water was added into the mixture to be extracted, and the resultant was columned using the developing solvent of hexane such that compound G of white solid was obtained.

(4) Compound H

[Reaction Formula 10-4]

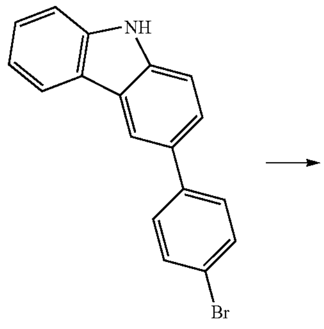

G

-continued

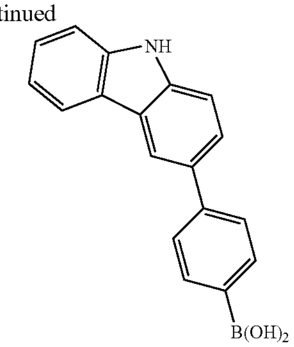

H

In the $N_2$ gas purging system, compound G, Bu—Li of 1.5 equivalent were put into ether, and the mixture was stirred under a temperature of −78° C. After completion of the reaction for 4 hours, triethyl borate of 1.2 equivalent was added, and the mixture was stirred for 30 minutes under a temperature of −78° C. The reaction temperature was raised in room temperature by removing a dry-ice bath. After completion of the reaction for 16 hours, HCl (30 ml) diluted by DI water was added to remove the organic solvent. After completely removing the organic solvent, the white solid, which is precipitated in water, was filtered such that compound H was obtained.

(5) Compound J

[Reaction Formula 10-5]

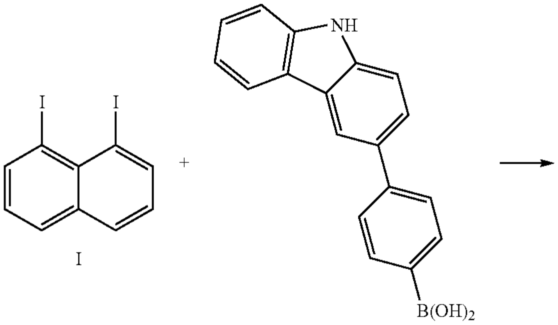

I H

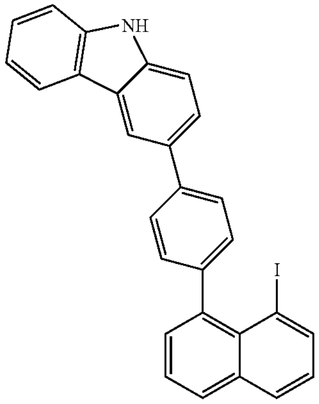

J

In the $N_2$ gas purging system, compound I, compound H of 0.9 equivalent, Pd(0) of 0.05 equivalent, and potassium carbonate of 4.0 equivalent were put into toluene, and the mixture was stirred in an oil bath under a temperature of 80° C. 8 hours after, water was added into the mixture to be extracted, and the resultant was columned using the developing solvent of hexane such that compound J of white solid was obtained.

(6) Compound 10

[Reaction Formula 10-6]

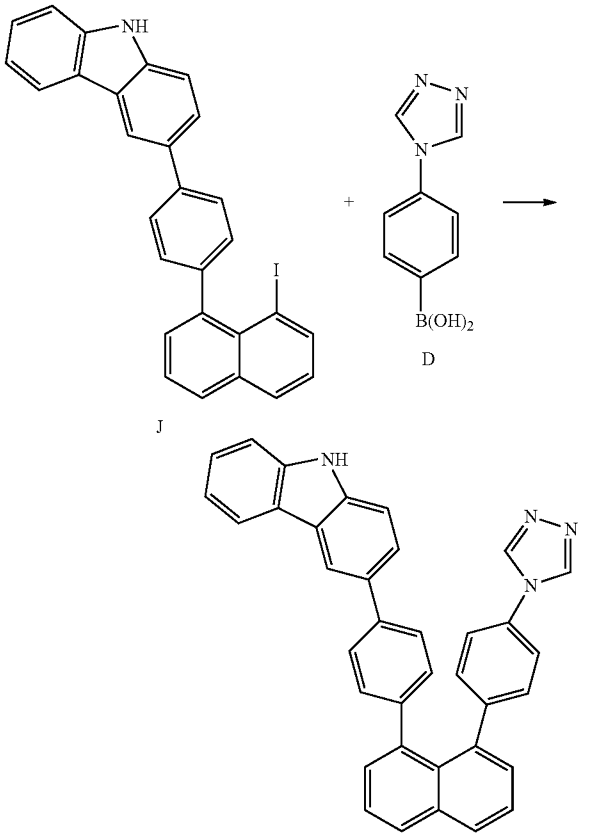

J

D

In the $N_2$ gas purging system, compound J, compound D of 1.2 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methylene chloride (7:3) such that the compound 10 of white solid was obtained.

11. Synthesis of Compound 11

(1) Compound C

[Reaction Formula 11-1]

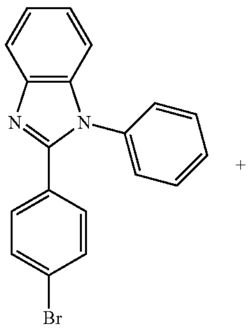

A

-continued

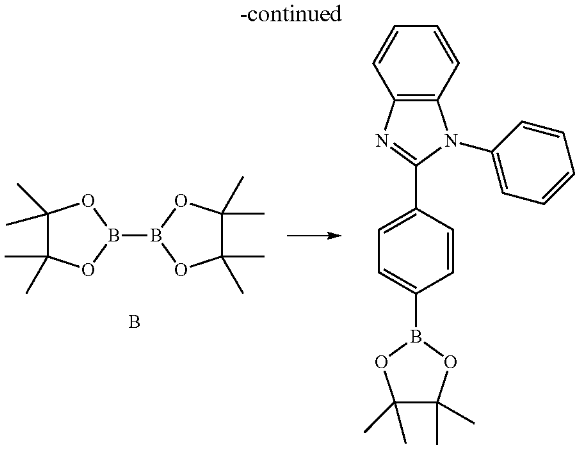

B

C

In the $N_2$ gas purging system, compound A, Bu—Li of 1.5 equivalent were put into ether, and the mixture was stirred under a temperature of −78° C. After completion of the reaction for 2 hours, compound B of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound C was obtained.

(2) Compound E

[Reaction Formula 11-2]

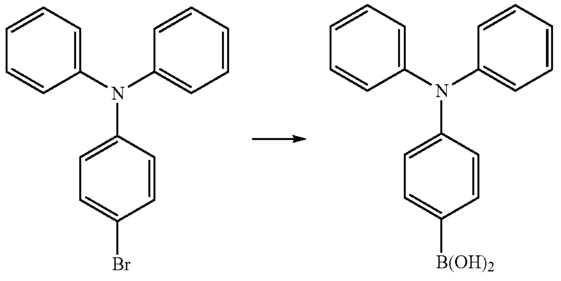

D

E

In the $N_2$ gas purging system, compound D, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound E was obtained.

(3) Compound G

[Reaction Formula 11-3]

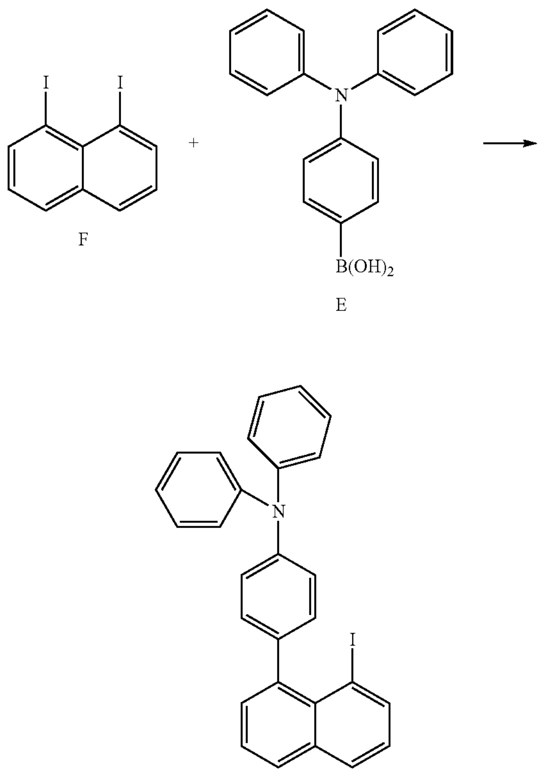

F E G

In the $N_2$ gas purging system, compound F, compound E of 0.9 equivalent, Pd(0) of 0.05 equivalent and potassium carbonate of 4.0 equivalent were put into toluene, and the mixture was stirred in an oil bath under a temperature of 80° C. 12 hours after, water was added into the mixture to be extracted, and the resultant was columned using the developing solvent of hexane such that compound G of white solid was obtained.

(4) Compound 11

[Reaction Formula 11-4]

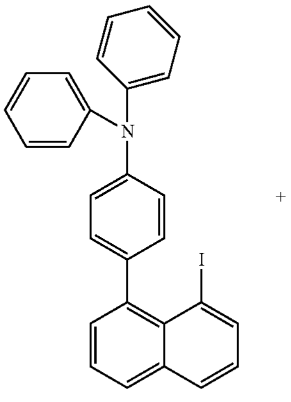

G

-continued

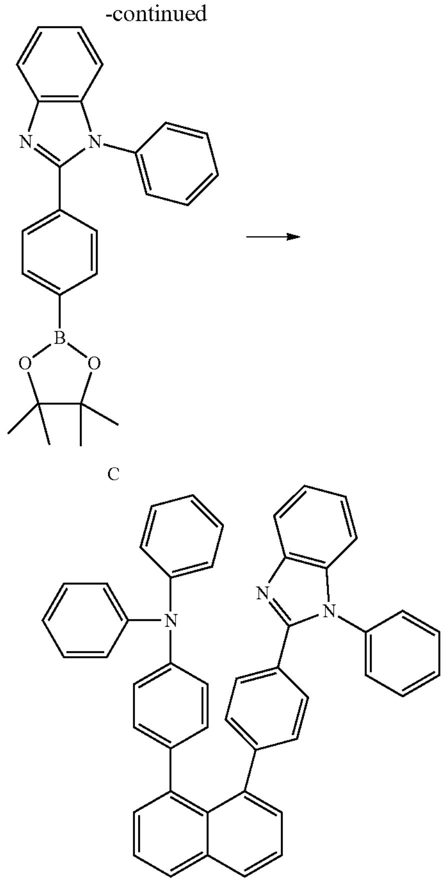

C

In the $N_2$ gas purging system, compound G, compound C of 1.2 equivalent, Pd(0) of 0.05 equivalent and potassium carbonate of 4.0 equivalent were put into toluene, and the mixture was stirred in an oil bath under a temperature of 80° C. 18 hours after, water was added into the mixture to be extracted, and the resultant was columned using the developing solvent of hexane and methylene chloride (6:4) such that the compound 11 of white solid was obtained.

12. Synthesis of Compound 12

(1) Compound C

[Reaction Formula 12-1]

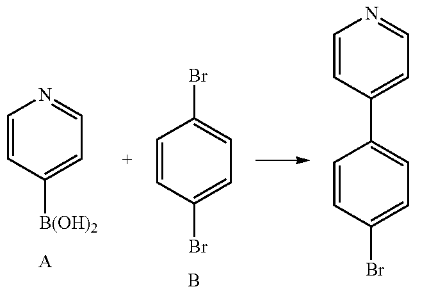

A B C

In the $N_2$ gas purging system, compound A, compound B of 0.9 equivalent, Pd(0) of 0.05 equivalent and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methyl chloride (2:1) such that compound C of white solid was obtained.

(2) Compound D

[Reaction Formula 12-2]

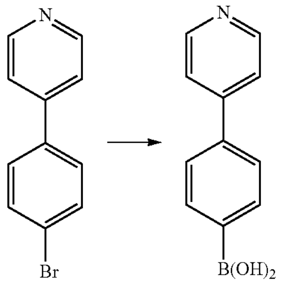

C D

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound E

[Reaction Formula 12-3]

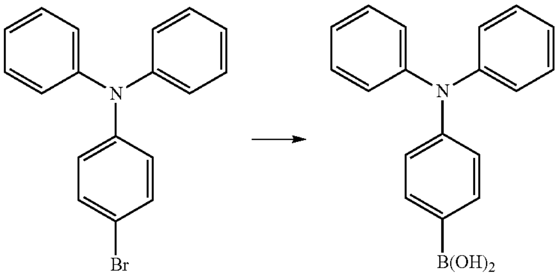

D1 E

In the $N_2$ gas purging system, compound D1, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound E was obtained.

(4) Compound G

[Reaction Formula 12-4]

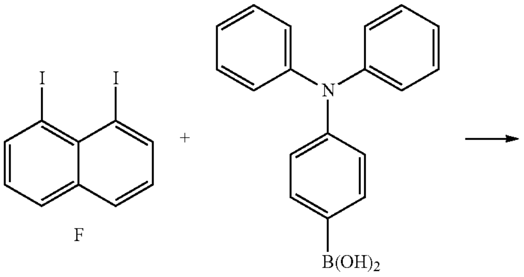

F E

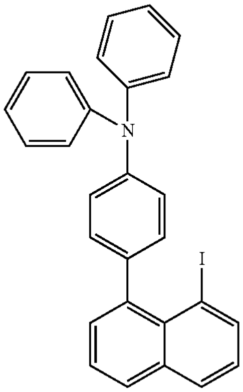

G

In the $N_2$ gas purging system, compound F, compound E of 0.9 equivalent, Pd(0) of 0.05 equivalent and potassium carbonate of 4.0 equivalent were put into toluene, and the mixture was stirred in an oil bath under a temperature of 80° C. 12 hours after, water was added into the mixture to be extracted, and the resultant was columned using the developing solvent of hexane such that compound G of white solid was obtained.

(5) Compound 12

[Reaction Formula 12-5]

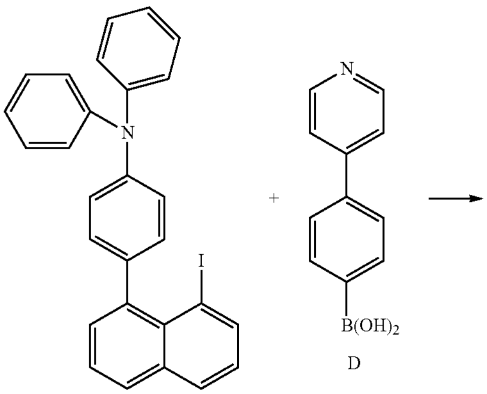

G D

-continued

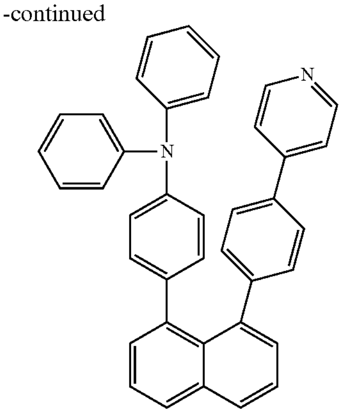

In the $N_2$ gas purging system, compound G, compound D of 1.2 equivalent, Pd(0) of 0.05 equivalent and potassium carbonate of 4.0 equivalent were put into toluene, and the mixture was stirred in an oil bath under a temperature of 80° C. 18 hours after, water was added into the mixture to be extracted, and the resultant was columned using the developing solvent of hexane and methylene chloride (8:2) such that the compound 12 of white solid was obtained.

13. Synthesis of Compound 13

(1) Compound C

[Reaction Formula 13-1]

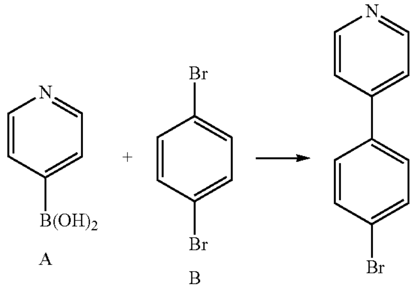

A B C

In the $N_2$ gas purging system, compound A, compound B of 0.9 equivalent, Pd(0) of 0.05 equivalent and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methyl chloride (2:1) such that compound C of white solid was obtained.

(2) Compound D

[Reaction Formula 13-2]

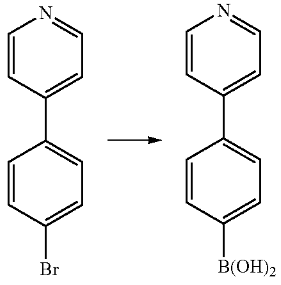

C D

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound G

[Reaction Formula 13-3]

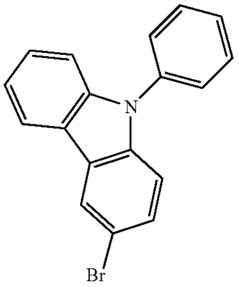

E

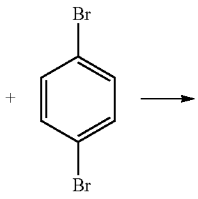

F

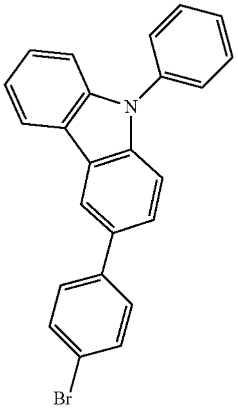

G

In the $N_2$ gas purging system, compound E, compound F of 0.9 equivalent, Pd(0) of 0.05 equivalent and potassium carbonate of 4.0 equivalent were put into toluene, and the mixture was stirred in an oil bath under a temperature of 80° C. 12 hours after, water was added into the mixture to be extracted, and the resultant was columned using the developing solvent of hexane such that compound G of white solid was obtained.

(4) Compound H

[Reaction Formula 13-4]

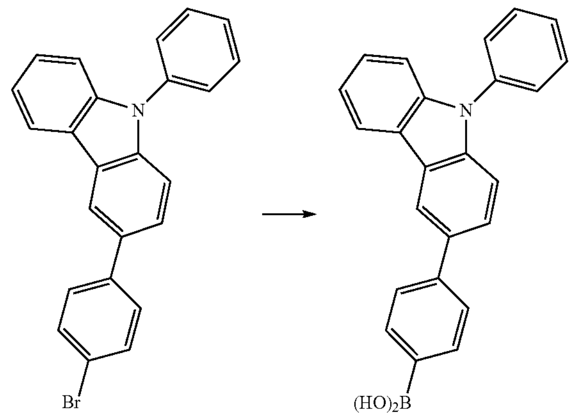

G H

In the $N_2$ gas purging system, compound G, Bu—Li of 1.5 equivalent were put into ether, and the mixture was stirred under a temperature of −78° C. After completion of the reaction for 4 hours, triethyl borate of 1.2 equivalent was added, and the mixture was stirred for 30 minutes under a temperature of −78° C. The reaction temperature was raised in room temperature by removing a dry-ice bath. After completion of the reaction for 16 hours, HCl (30 ml) diluted by DI water was added to remove the organic solvent. After completely removing the organic solvent, the white solid, which is precipitated in water, was filtered such that compound H was obtained.

(5) Compound J

[Reaction Formula 13-5]

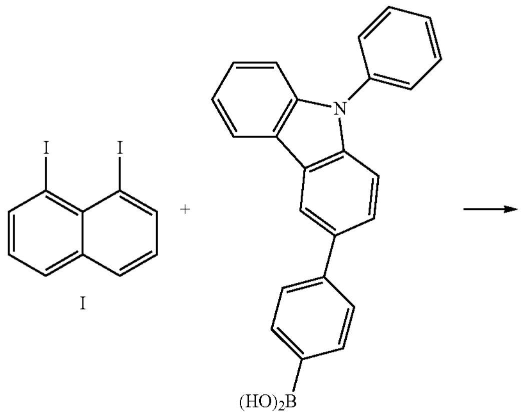

I H

-continued

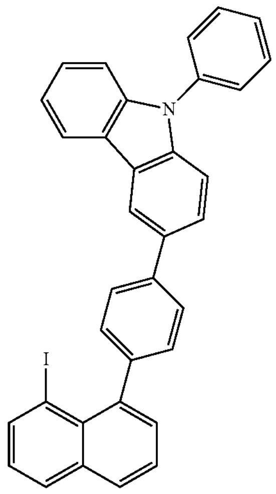

J

In the $N_2$ gas purging system, compound I, compound H of 0.9 equivalent, Pd(0) of 0.05 equivalent and potassium carbonate of 4.0 equivalent were put into toluene, and the mixture was stirred in an oil bath under a temperature of 80° C. 8 hours after, water was added into the mixture to be extracted, and the resultant was columned using the developing solvent of hexane such that compound J of white solid was obtained.

(6) Compound 13

[Reaction Formula 13-6]

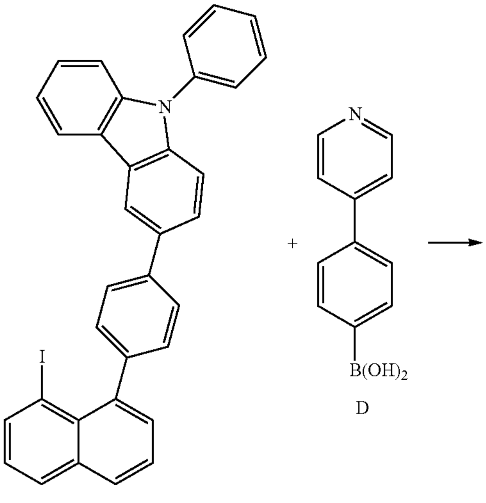

J D

-continued

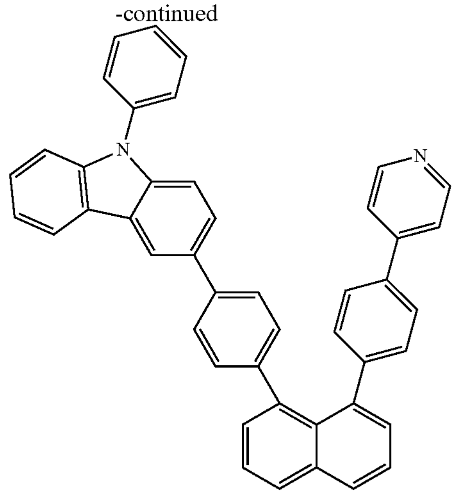

In the $N_2$ gas purging system, compound J, compound D of 1.2 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and ethylene acetate (8:2) such that the compound 13 of white solid was obtained.

14. Synthesis of Compound 14

(1) Compound C

[Reaction Formula 14-1]

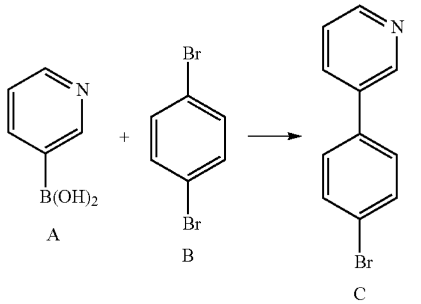

A B C

In the $N_2$ gas purging system, compound A, compound B of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methyl chloride (2:1) such that compound C of white solid was obtained.

(2) Compound D

[Reaction Formula 14-2]

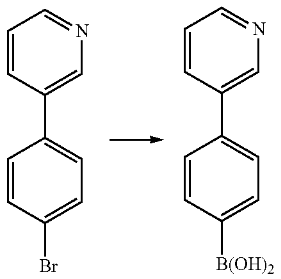

C D

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound G

[Reaction Formula 14-3]

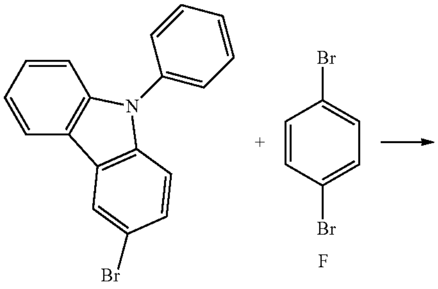

E F

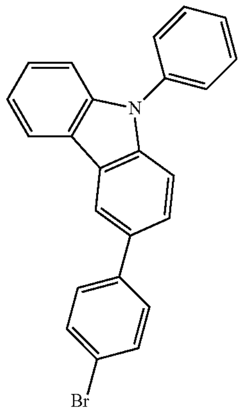

G

In the $N_2$ gas purging system, compound E, compound F of 0.9 equivalent, Pd(0) of 0.05 equivalent, and potassium carbonate of 4.0 equivalent were put into toluene, and the mixture was stirred in an oil bath under a temperature of 80°

C. 12 hours after, water was added into the mixture to be extracted, and the resultant was columned using the developing solvent of hexane such that compound G of white solid was obtained.

(4) Compound H

[Reaction Formula 14-4]

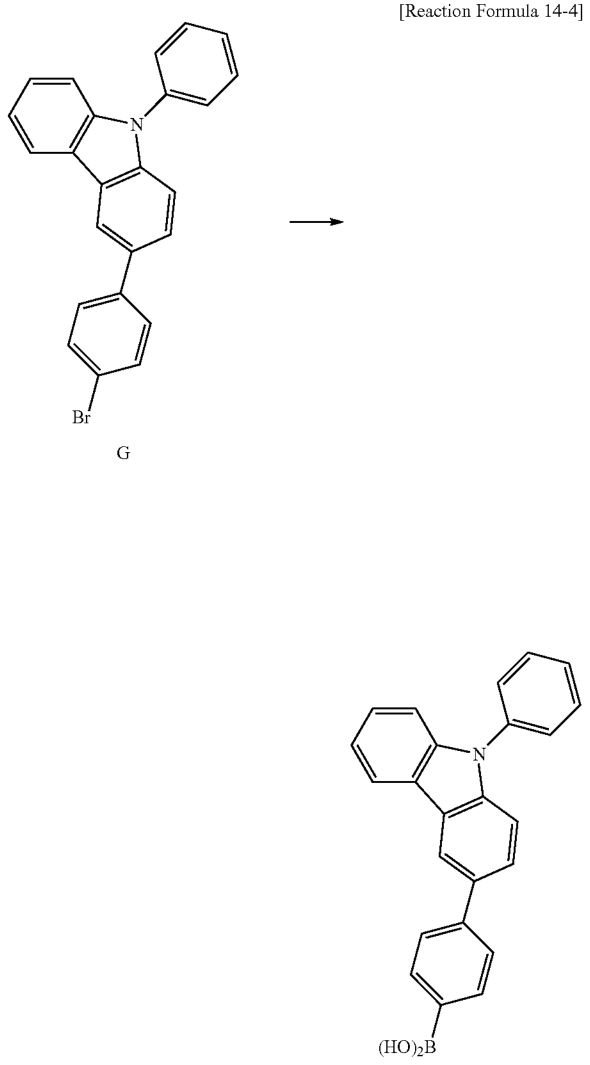

G H

In the $N_2$ gas purging system, compound G, Bu—Li of 1.5 equivalent were put into ether, and the mixture was stirred under a temperature of −78° C. After completion of the reaction for 4 hours, triethyl borate of 1.2 equivalent was added, and the mixture was stirred for 30 minutes under a temperature of −78° C. The reaction temperature was raised in room temperature by removing a dry-ice bath. After completion of the reaction for 16 hours, HCl (30 ml) diluted by DI water was added to remove the organic solvent. After completely removing the organic solvent, the white solid, which is precipitated in water, was filtered such that compound H was obtained.

(5) Compound J

[Reaction Formula 14-5]

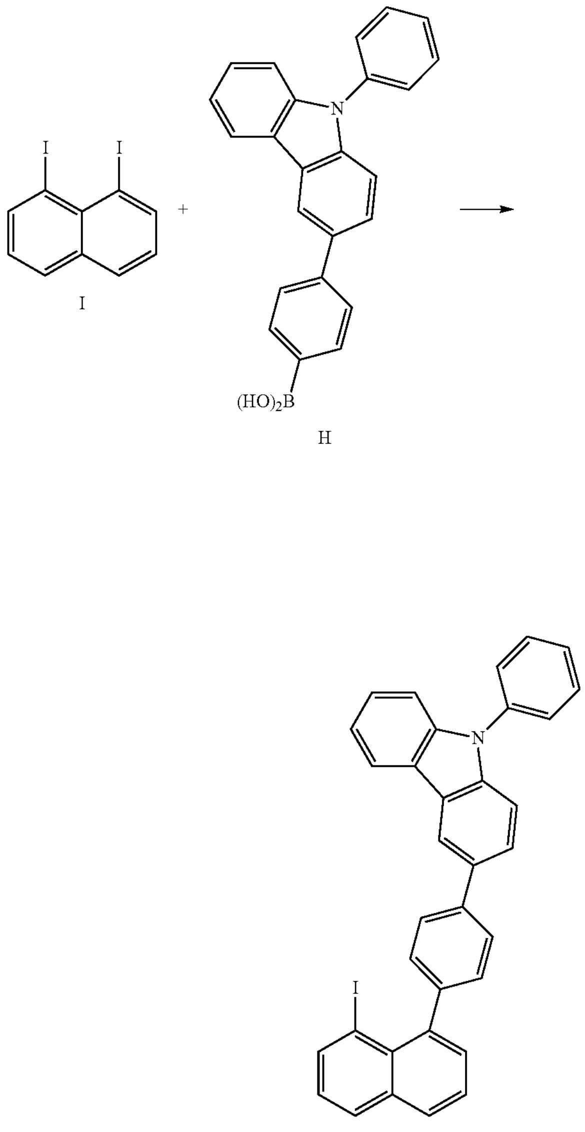

I H J

In the $N_2$ gas purging system, compound I, compound H of 0.9 equivalent, Pd(0) of 0.05 equivalent and potassium carbonate of 4.0 equivalent were put into toluene, and the mixture was stirred in an oil bath under a temperature of 80° C. 8 hours after, water was added into the mixture to be extracted, and the resultant was columned using the developing solvent of hexane such that compound J of white solid was obtained.

(6) Compound 14

[Reaction Formula 14-6]

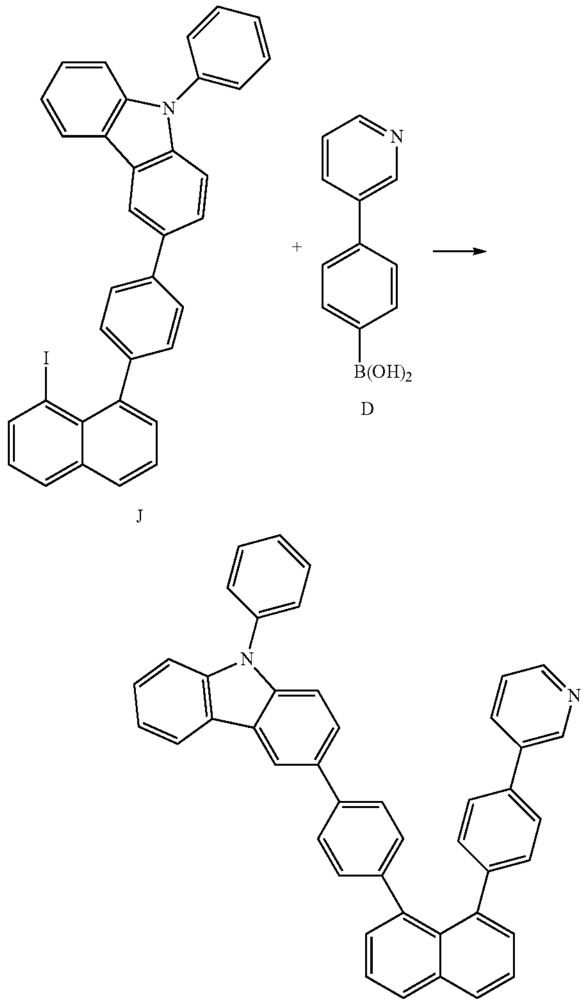

J

D

In the $N_2$ gas purging system, compound J, compound D of 1.2 equivalent, Pd(0) of 0.05 equivalent and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and ethylene acetate (8:2) such that the compound 14 of white solid was obtained.

15. Synthesis of Compound 15

(1) Compound C

[Reaction Formula 15-1]

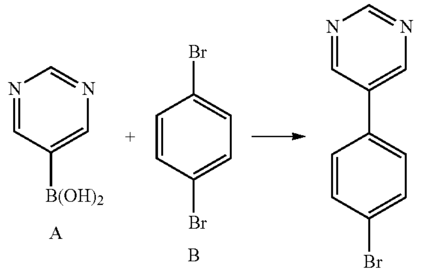

A B C

In the $N_2$ gas purging system, compound A, compound B of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methyl chloride (2:1) such that compound C of white solid was obtained.

(2) Compound D

[Reaction Formula 15-2]

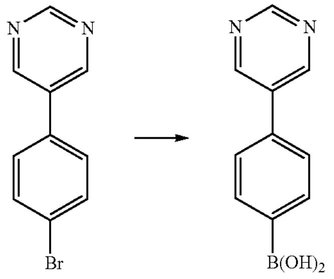

C D

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound G

[Reaction Formula 15-3]

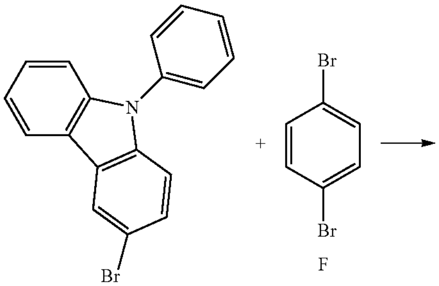

E F

-continued

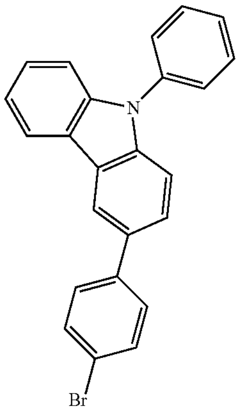

G

In the $N_2$ gas purging system, compound E, compound F of 0.9 equivalent, Pd(0) of 0.05 equivalent, and potassium carbonate of 4.0 equivalent were put into toluene, and the mixture was stirred in an oil bath under a temperature of 80° C. 12 hours after, water was added into the mixture to be extracted, and the resultant was columned using the developing solvent of hexane such that compound G of white solid was obtained.

(4) Compound H

[Reaction Formula 15-4]

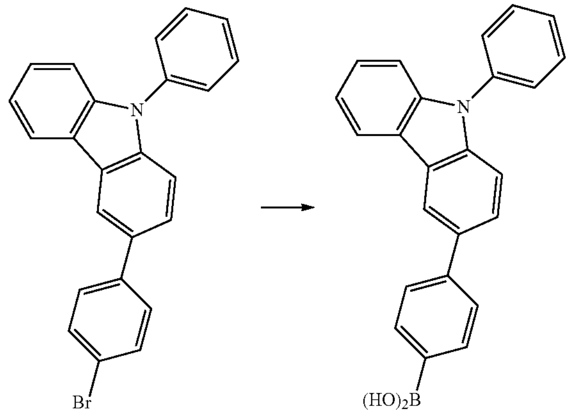

G H

In the $N_2$ gas purging system, compound G, Bu—Li of 1.5 equivalent were put into ether, and the mixture was stirred under a temperature of −78° C. After completion of the reaction for 4 hours, triethyl borate of 1.2 equivalent was added, and the mixture was stirred for 30 minutes under a temperature of −78° C. The reaction temperature was raised in room temperature by removing a dry-ice bath. After completion of the reaction for 16 hours, HCl (30 ml) diluted by DI water was added to remove the organic solvent. After completely removing the organic solvent, the white solid, which is precipitated in water, was filtered such that compound H was obtained.

(5) Compound J

[Reaction Formula 15-5]

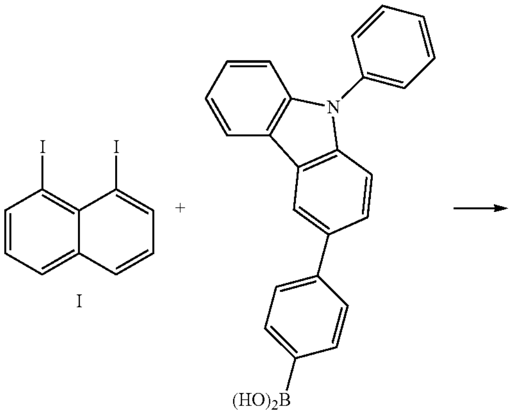

I H

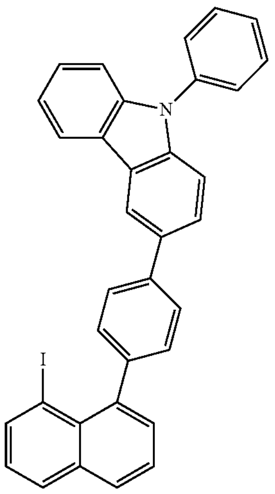

J

In the $N_2$ gas purging system, compound I, compound H of 0.9 equivalent, Pd(0) of 0.05 equivalent, and potassium carbonate of 4.0 equivalent were put into toluene, and the mixture was stirred in an oil bath under a temperature of 80° C. 8 hours after, water was added into the mixture to be extracted, and the resultant was columned using the developing solvent of hexane such that compound J of white solid was obtained.

(6) Compound 15

[Reaction Formula 15-6]

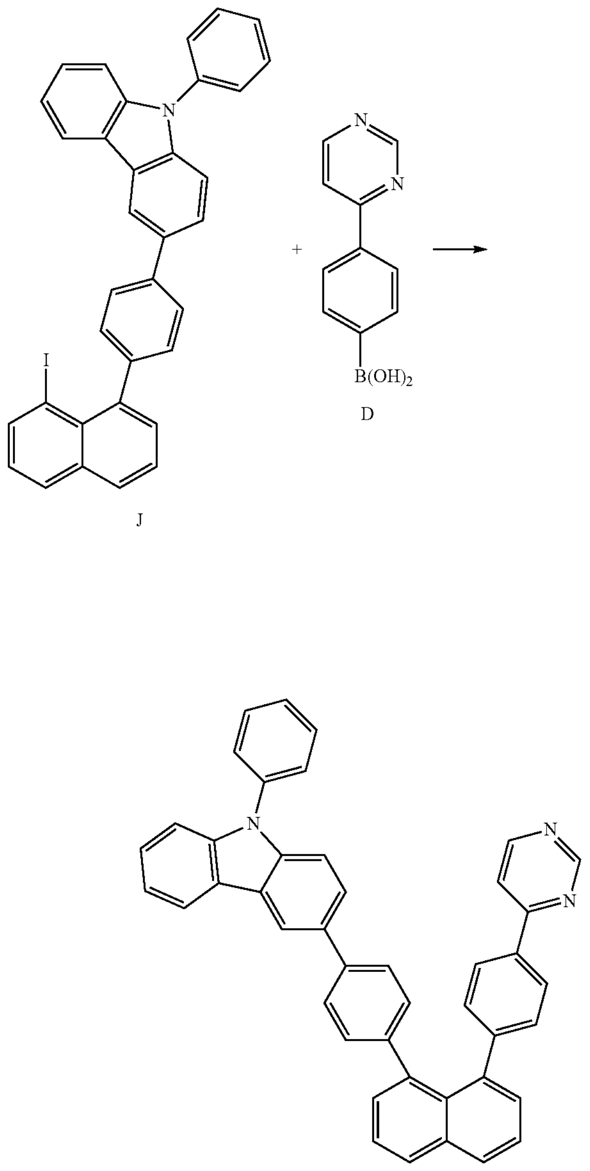

J

D

In the $N_2$ gas purging system, compound J, compound D of 1.2 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and ethylene acetate (9:1) such that the compound 15 of white solid was obtained.

16. Synthesis of Compound 16

(1) Compound C

[Reaction Formula 16-1]

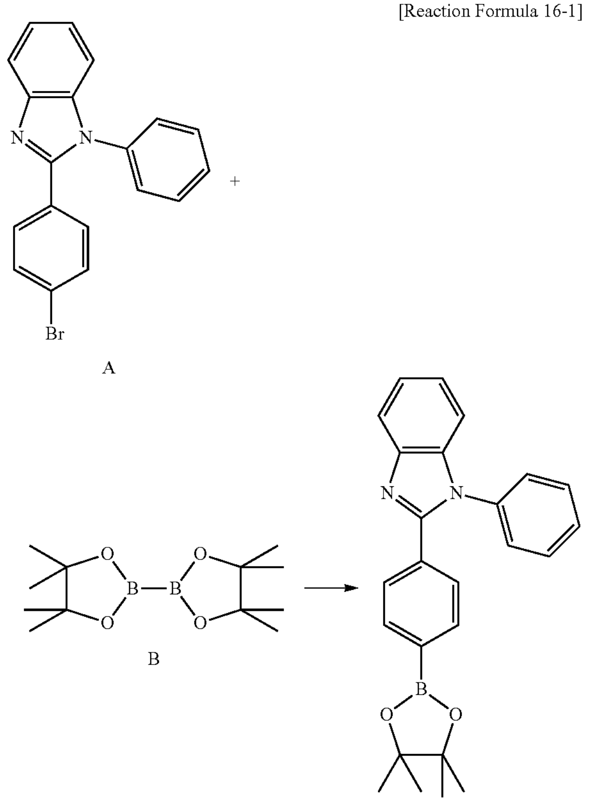

A

B

C

In the $N_2$ gas purging system, compound A, Bu—Li of 1.5 equivalent were put into ether, and the mixture was stirred under a temperature of −78° C. After completion of the reaction for 2 hours, compound B of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound C was obtained.

(2) Compound F

[Reaction Formula 16-2]

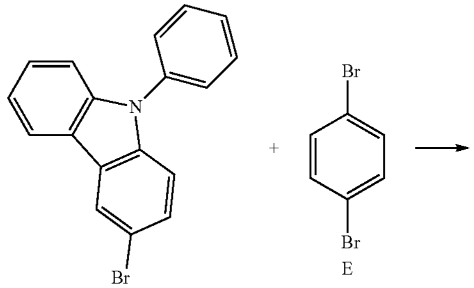

D

E

-continued

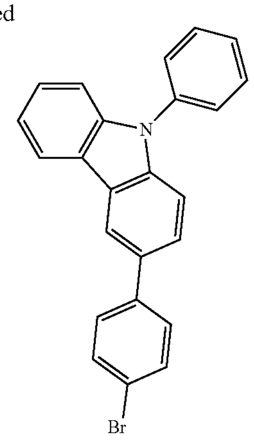

F

In the $N_2$ gas purging system, compound D, compound E of 0.9 equivalent, Pd(0) of 0.05 equivalent, and potassium carbonate of 4.0 equivalent were put into toluene, and the mixture was stirred in an oil bath under a temperature of 80° C. 12 hours after, water was added into the mixture to be extracted, and the resultant was columned using the developing solvent of hexane such that compound F of white solid was obtained.

(3) Compound G

[Reaction Formula 16-3]

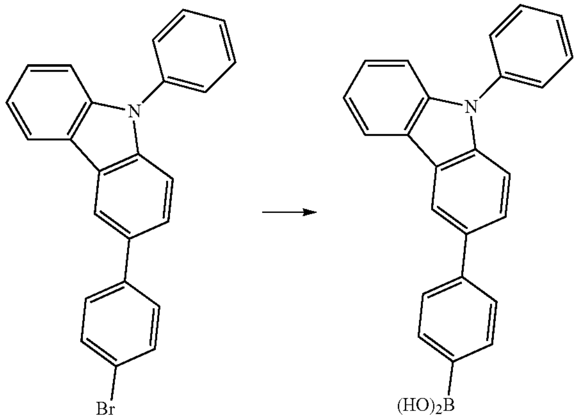

F G

In the $N_2$ gas purging system, compound F, Bu—Li of 1.5 equivalent were put into ether, and the mixture was stirred under a temperature of −78° C. After completion of the reaction for 4 hours, triethyl borate of 1.2 equivalent was added, and the mixture was stirred for 30 minutes under a temperature of −78° C. The reaction temperature was raised in room temperature by removing a dry-ice bath. After completion of the reaction for 16 hours, HCl (30 ml) diluted by DI water was added to remove the organic solvent. After completely removing the organic solvent, the white solid, which is precipitated in water, was filtered such that compound G was obtained.

(4) Compound I

[Reaction Formula 16-4]

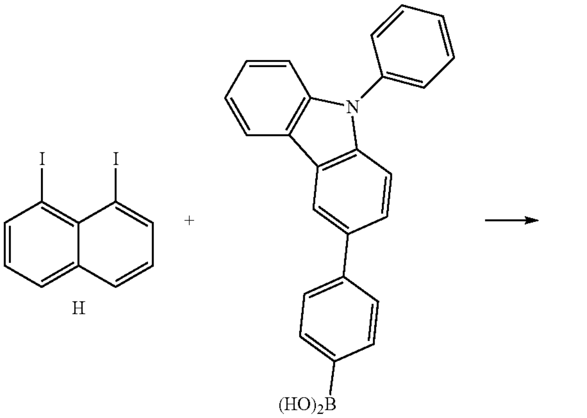

G

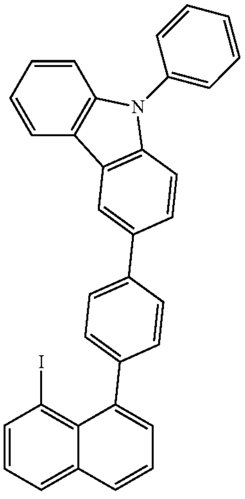

I

In the $N_2$ gas purging system, compound H, compound G of 0.9 equivalent, Pd(0) of 0.05 equivalent, and potassium carbonate of 4.0 equivalent were put into toluene, and the mixture was stirred in an oil bath under a temperature of 80° C. 8 hours after, water was added into the mixture to be extracted, and the resultant was columned using the developing solvent of hexane such that compound I of white solid was obtained.

(5) Compound 16

[Reaction Formula 16-5]

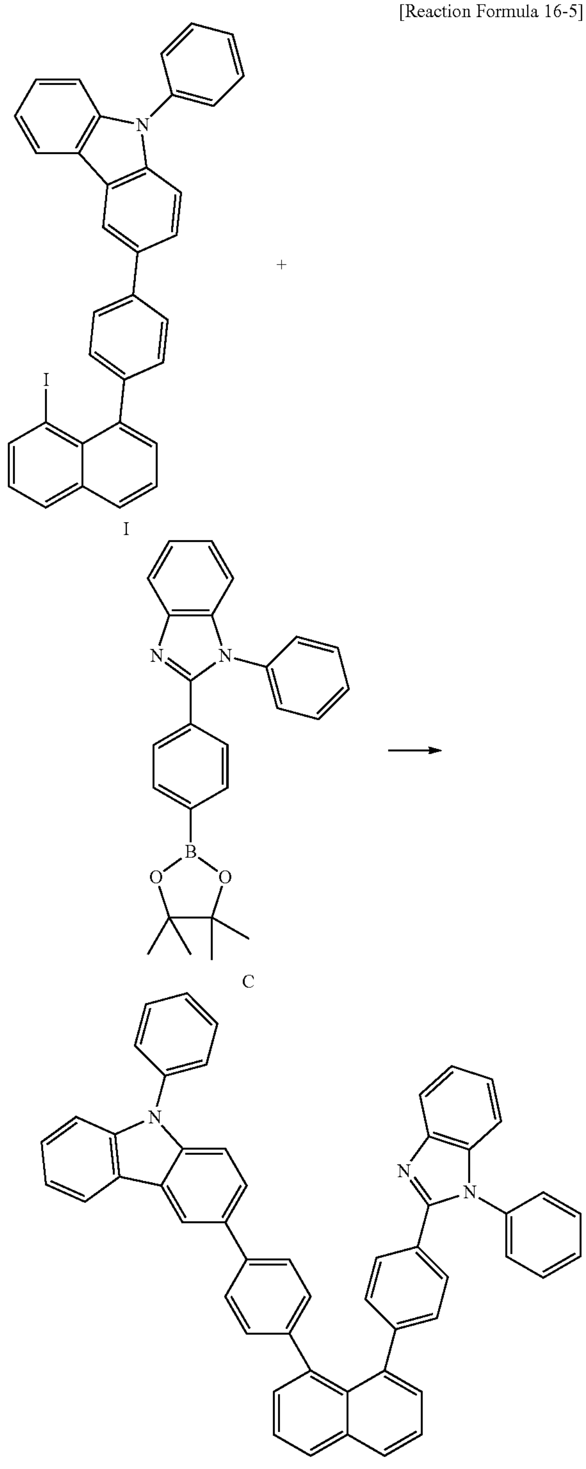

I

C

In the $N_2$ gas purging system, compound I, compound C of 1.2 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and ethylene acetate (9:1) such that the compound 16 of white solid was obtained.

17. Synthesis of Compound 17

(1) Compound C

[Reaction Formula 17-1]

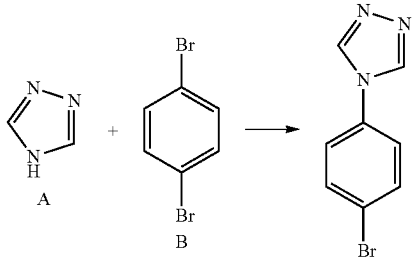

A B C

In the $N_2$ gas purging system, compound A, compound B of 0.9 equivalent, Pd(0) of 0.05 equivalent, and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane such that compound C of white solid was obtained.

(2) Compound D

[Reaction Formula 17-2]

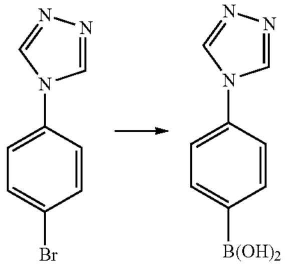

C D

In the $N_2$ gas purging system, compound C, Bu—Li of 1.5 equivalent were put into ether, and the mixture was stirred under a temperature of −78° C. After completion of the reaction for 2 hours, triethyl borate of 1.2 equivalent was added, and the mixture was stirred for 30 minutes under a temperature of −78° C. The reaction temperature was raised in room temperature by removing a dry-ice bath. After completion of the reaction for 8 hours, HCl (30 ml) diluted by DI water was added to remove the organic solvent. After completely removing the organic solvent, the white solid, which is precipitated in water, was filtered such that compound D was obtained.

(3) Compound G

[Reaction Formula 17-3]

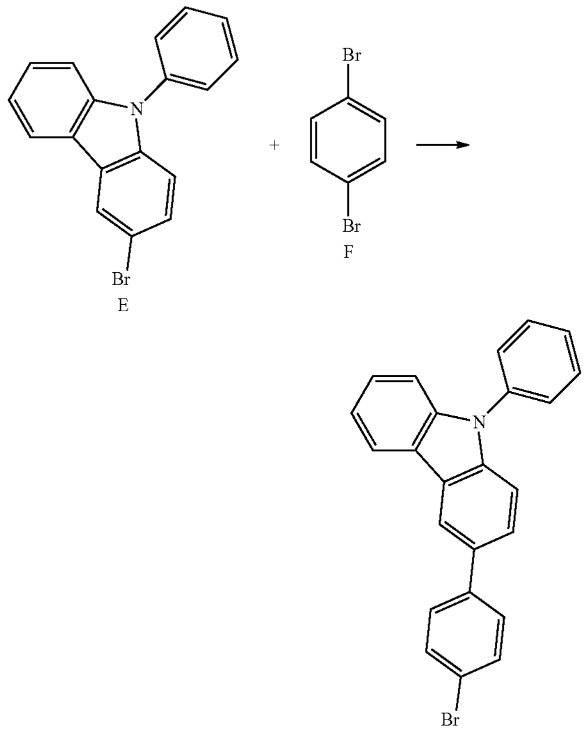

E F G

In the $N_2$ gas purging system, compound E, compound F of 0.9 equivalent, Pd(0) of 0.05 equivalent, and potassium carbonate of 4.0 equivalent were put into toluene, and the mixture was stirred in an oil bath under a temperature of 80° C. 12 hours after, water was added into the mixture to be extracted, and the resultant was columned using the developing solvent of hexane such that compound G of white solid was obtained.

(4) Compound H

[Reaction Formula 17-4]

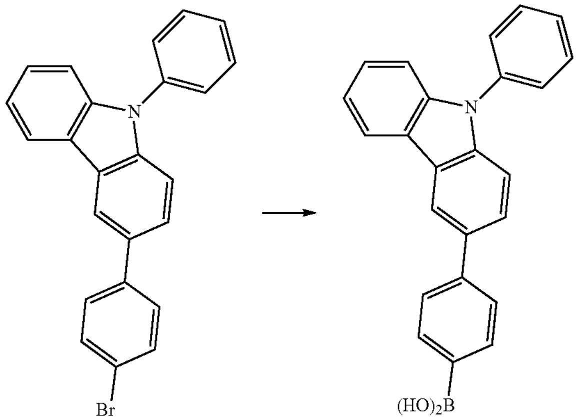

G H

In the $N_2$ gas purging system, compound G, Bu—Li of 1.5 equivalent were put into ether, and the mixture was stirred under a temperature of −78° C. After completion of the reaction for 4 hours, triethyl borate of 1.2 equivalent was added, and the mixture was stirred for 30 minutes under a temperature of −78° C. The reaction temperature was raised in room temperature by removing a dry-ice bath. After completion of the reaction for 16 hours, HCl (30 ml) diluted by DI water was added to remove the organic solvent. After completely removing the organic solvent, the white solid, which is precipitated in water, was filtered such that compound H was obtained.

(5) Compound J

[Reaction Formula 17-5]

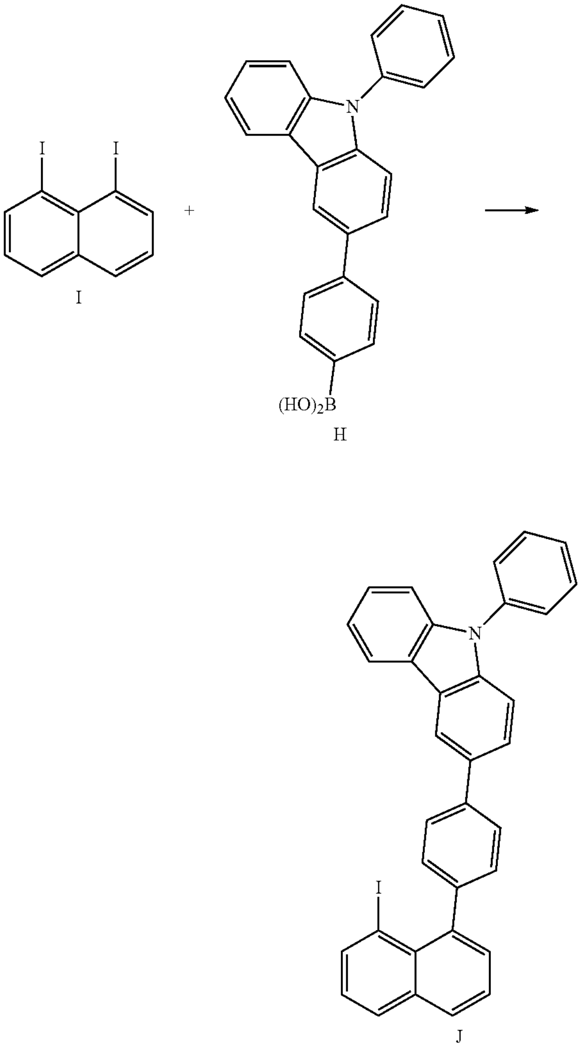

I H J

In the $N_2$ gas purging system, compound I, compound H of 0.9 equivalent, Pd(0) of 0.05 equivalent and potassium carbonate of 4.0 equivalent were put into toluene, and the mixture was stirred in an oil bath under a temperature of 80° C. 8 hours after, water was added into the mixture to be extracted, and the resultant was columned using the developing solvent of hexane such that compound J of white solid was obtained.

(6) Compound 17

[Reaction Formula 17-6]

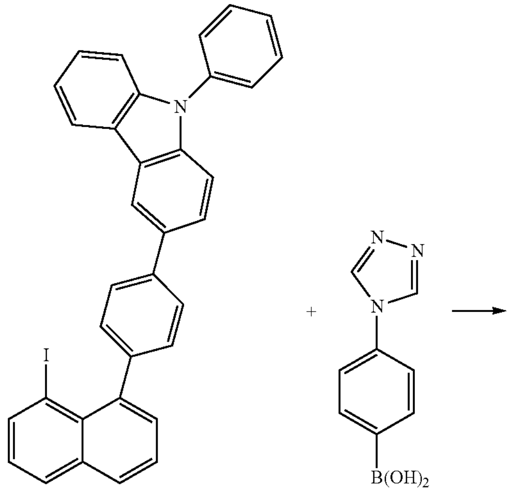

J D

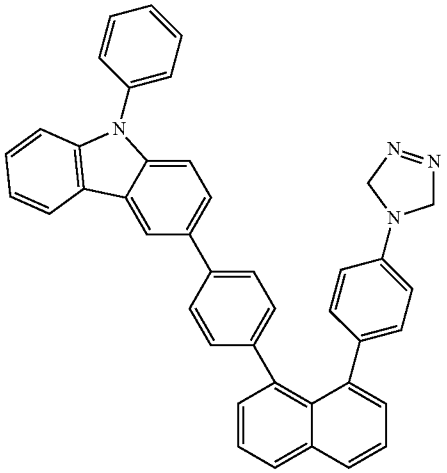

In the $N_2$ gas purging system, compound J, compound D of 1.2 equivalent, Pd(0) of 0.05 equivalent and potassium carbonate of 4.0 equivalent were put into toluene, and the mixture was stirred in an oil bath under a temperature of 80° C. 16 hours after, water was added into the mixture to be extracted, and the resultant was columned using the developing solvent of hexane and methylene chloride (7:3) such that the compound 17 of white solid was obtained.

The maximum absorption peak (MAP), the maximum emission peak (MEP), and Stocks-shift value of the above compounds 1 and 2 and reference compounds in Formulas 5 and 6 are listed in Tables 2 to 5, respectively.

[Formula 5]

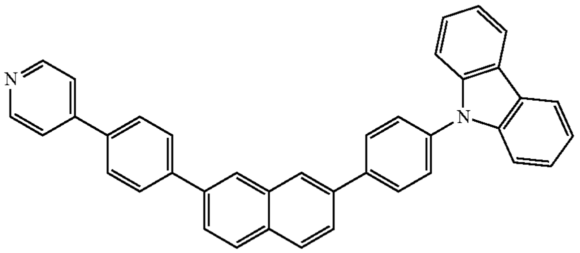

[Formula 6]

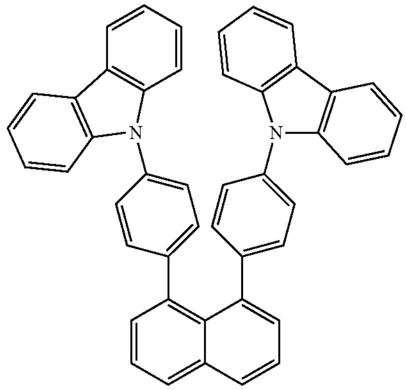

TABLE 2

| Solvent | Δf | MAP $cm^{-1}$ (nm) | MEP $cm^{-1}$ (nm) | Stock shift $cm^{-1}$ |
|---|---|---|---|---|
| $CHCl_3$ | 0.1492 | 30120 (332) | 21413 (467) | 8707 |
| Toluene | 0.0159 | 30120 (332) | 23057 (433) | 7063 |
| Mx1[a)] | 0.0730 | 30120 (332) | 22320 (448) | 7800 |
| MX2[b)] | 0.1798 | 30120 (332) | 21163 (472) | 8957 |
| MX3[c)] | 0.1131 | 30120 (332) | 21961 (455) | 8159 |
| MX4[d)] | 0.1035 | 30120 (332) | 22063 (453) | 8057 |

[a)]Mx1, mixed solvent of $CHCl_3$/Cyclohexane = 1/1,
[b)]MX2, Mixed solvent of $CHCl_3$/THF = 1/1,
[c)]MX3, Mixed solvent of Toluene/THF = 1/1,
[d)]MX4, Mixed solvent of $CHCl_3$/THF = 1/1

TABLE 3

| Solvent | Δf | MAP $cm^{-1}$ (nm) | MEP $cm^{-1}$ (nm) | Stock shift $cm^{-1}$ |
|---|---|---|---|---|
| $CHCl_3$ | 0.1492 | 30303 (330) | 21616 (462) | 8687 |
| Toluene | 0.0159 | 30303 (330) | 23331 (428) | 6972 |
| Mx1[a)] | 0.0730 | 30303 (330) | 22298 (448) | 8005 |
| MX2[b)] | 0.1798 | 30303 (330) | 21441 (466) | 8862 |
| MX3[c)] | 0.1131 | 30303 (330) | 22034 (453) | 8269 |
| MX4[d)] | 0.1035 | 30303 (330) | 22155 (451) | 8148 |

[a)]Mx1, mixed solvent of $CHCl_3$/Cyclohexane = 1/1,
[b)]MX2, Mixed solvent of $CHCl_3$/THF = 1/1,
[c)]MX3, Mixed solvent of Toluene/THF = 1/1,
[d)]MX4, Mixed solvent of $CHCl_3$/THF = 1/1

TABLE 4

| Solvent | Δf | MAP $cm^{-1}$ (nm) | MEP $cm^{-1}$ (nm) | Stock shift $cm^{-1}$ |
|---|---|---|---|---|
| $CHCl_3$ | 0.1492 | 28985 (345) | 19958 (501) | 9027 |
| Toluene | 0.0159 | 28985 (345) | 22485 (444) | 6500 |
| Mx1[a)] | 0.0730 | 28985 (345) | 21826 (458) | 7159 |

TABLE 4-continued

| Solvent | Δf | MAP $cm^{-1}$ (nm) | MEP $cm^{-1}$ (nm) | Stock shift $cm^{-1}$ |
|---|---|---|---|---|
| MX2[b)] | 0.1798 | 28985 (345) | 20069 (498) | 8916 |
| MX3[c)] | 0.1131 | 28985 (345) | 21182 (472) | 7803 |
| MX4[d)] | 0.1035 | 28985 (345) | 21160 (472) | 7825 |

[a)]Mx1, mixed solvent of $CHCl_3$/Cyclohexane = 1/1,
[b)]MX2, Mixed solvent of $CHCl_3$/THF = 1/1,
[c)]MX3, Mixed solvent of Toluene/THF = 1/1,
[d)]MX4, Mixed solvent of $CHCl_3$/THF = 1/1

TABLE 5

| Solvent | Δf | MAP $cm^{-1}$ (nm) | MEP $cm^{-1}$ (nm) | Stock shift $cm^{-1}$ |
|---|---|---|---|---|
| $CHCl_3$ | 0.1492 | 29411 (340) | 21739 (460) | 7672 |
| Toluene | 0.0159 | 29411 (340) | 23201 (431) | 6210 |
| Mx1[a)] | 0.0730 | 29411 (340) | 23041 (434) | 6370 |
| MX2[b)] | 0.1798 | 29411 (340) | 21834 (458) | 7577 |

TABLE 5-continued

| Solvent | Δf | MAP $cm^{-1}$ (nm) | MEP $cm^{-1}$ (nm) | Stock shift $cm^{-1}$ |
|---|---|---|---|---|
| MX3[c)] | 0.1131 | 29411 (340) | 22573 (443) | 6838 |
| MX4[d)] | 0.1035 | 29411 (340) | 22675 (441) | 6736 |

[a)]Mx1, mixed solvent of $CHCl_3$/Cyclohexane = 1/1,
[b)]MX2, Mixed solvent of $CHCl_3$/THF = 1/1,
[c)]MX3, Mixed solvent of Toluene/THF = 1/1,
[d)]MX4, Mixed solvent of $CHCl_3$/THF = 1/1

As listed in Table 2 and 3, the space-through charge transfer compounds of the present invention has the maximum absorption peak of 332 nm and 330 nm, respectively, regardless the kinds of the solvents, while the emission spectrums are various according to the kinds of the solvents. Namely, the space-through charge transfer compound of the present invention has a relatively low maximum emission peak in the solvent of toluene having a relatively low polarity and a relatively high maximum emission peak in the solvent of $CHCl_3$ and THF having a relatively low polarity. As a result, as the polarity of the solvent is increased, the maximum emission peak of the space-through charge transfer compound is red-shifted.

The emission properties of the above compounds 1 and 2 (Com1 and Com2) and the references compounds 1 and 2 (Ref1 and Ref2) in the Formulas 5 and 6 are measured and the results are listed in Table 6 and shown in FIGS. 3A to 3D. (Quantarus tau apparatus of Hamamatsu Co., Ltd. $O_2$ free condition.)

TABLE 6

| | Prompt (ns) | Delayed (ns) |
|---|---|---|
| 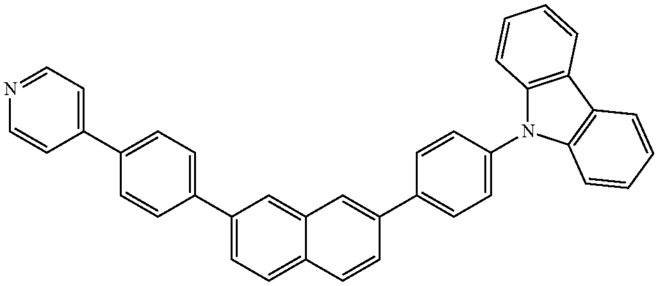 Ref1 | 3.95 | — |
| 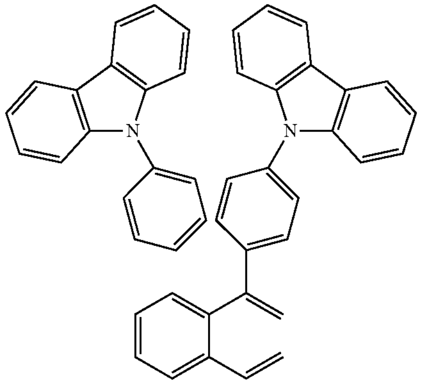 Ref2 | 2.79 | — |

TABLE 6-continued

| | Prompt (ns) | Delayed (ns) |
|---|---|---|
| 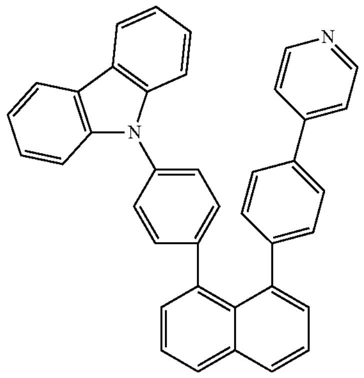 Com1 | 23.59 | 29967.9 |
| 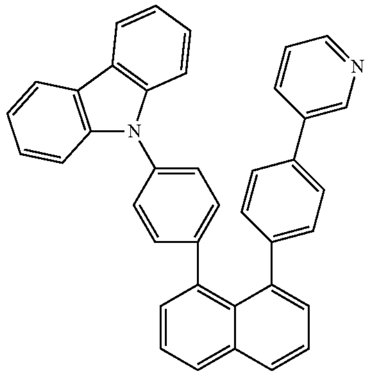 Com2 | 7.28 | 41171.2 |

Figure 3A:
FIGS. 3A to 3D are graphs showing a delayed fluorescent property of a space-through charge transfer compound, according to the present invention.
Figure 3B:
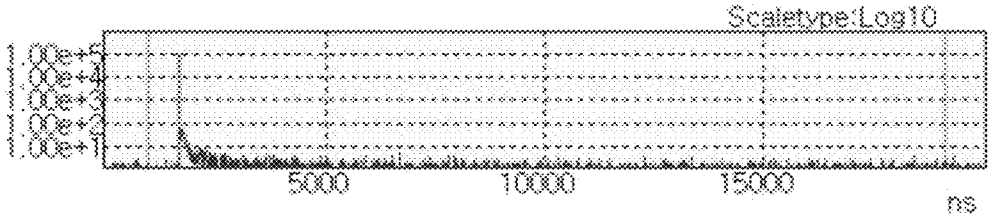
Figure 3C:
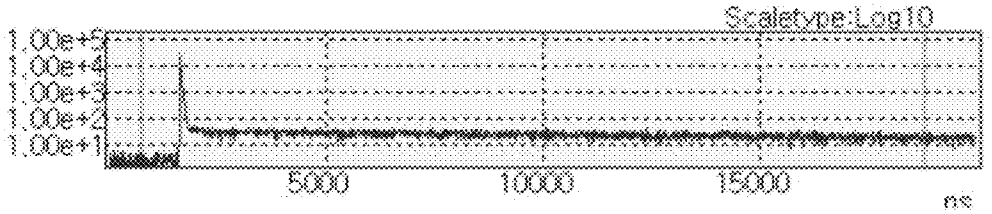
Figure 3D:
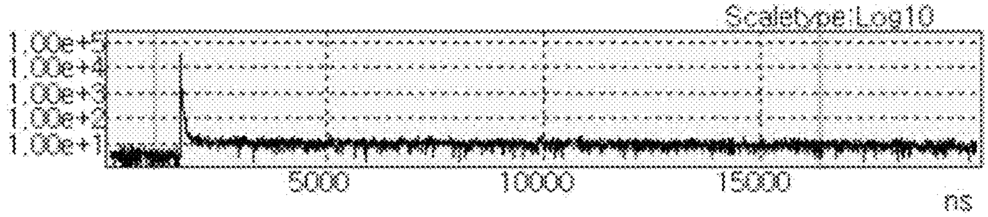

As shown in Table 6 and FIGS. 3A and 3B, the reference compounds (Ref1 and Ref2) only show the fluorescent emission (Prompt). However, as shown in Table 6 and FIGS. 3C and 3D, the space-through charge transfer compounds (Com1 and Com2) of the present invention show the delayed fluorescent emission (Delayed) of tens of thousands of nano-seconds (ns) with the fluorescent emission (Prompt).

As mentioned above, the space-through charge transfer compound of the present invention is activated by the field such that the excitons in the singlet state "$S_1$" and the triplet state "$T_1$" are transited into the intermediated state "$I_1$". As a result, both the exciton in the singlet state "$S_1$" and the exciton in the triplet state "$T_1$" are engaged in the emission.

The FADF compound is a single molecule compound having the electron donor moiety and the electron acceptor moiety in the single molecule such that the charge transfer is easily generated through a space in the molecule. In the FADF compound with particular conditions, the charge can be separated from the electron donor moiety to the electron acceptor moiety through the space between the electron donor moiety to the electron acceptor moiety.

The FADF compound is activated by outer factors. It can be verified by comparing the absorption peak and the emission peak of the solution of the compounds.

$$\Delta\nu = \nu abs - \nu fl = \frac{2\Delta\mu^2}{hca^3}\Delta f + \text{constant} \quad \text{(Lippert-Mataga equation)}$$

In the above equation, "Δυ" is the Stock-shift value, and "υabs" and "υfl" are the wave-number of the maximum absorption peak and the maximum emission peak, respectively. "h" is Planck's constant, "c" is the velocity of light, "a" is the onsager cavity radius, and "Δμ" is a difference between the dipole moment of the excited state and the dipole moment of the ground state. ($\Delta\mu=\mu_e-\mu_g$)

"Δf" is a value indicating the orientational polarizability of the solvent and may be a function of the dielectric constant of the solvent (ε) and the refractive index of the solvent (n).

$$\Delta f = \frac{\varepsilon - 1}{2\varepsilon + 1} - \frac{n^2 - 1}{2n^2 + 1}$$

Since the intensity of dipole moment in the excited state is determined by the peripheral polarity (e.g., the polarity of the solvent), the FADF can be verified by comparing the absorption peak and the emission peak of the solution of the compounds.

The orientational polarizability (Δf) of the mixed solvent can be calculated by using the orientational polarizability of each pure solvent and their mole fraction. When "Δf" and "Δυ" are linearly plotted by using above "Lippert-Mataga equation", the compound may provide the FADF emission.

Namely, when the FADF complex is stabilized according to the orientational polarizability of the solvent, the emission peak is shifted in a long wavelength according to the degree of the stabilization. Accordingly, when the compound provides the FADF emission, "Δf" and "Δυ" are plotted in a linear line. When "Δf" and "Δυ" are plotted in a linear line, the compound provides the FADF emission.

Figure 4A:
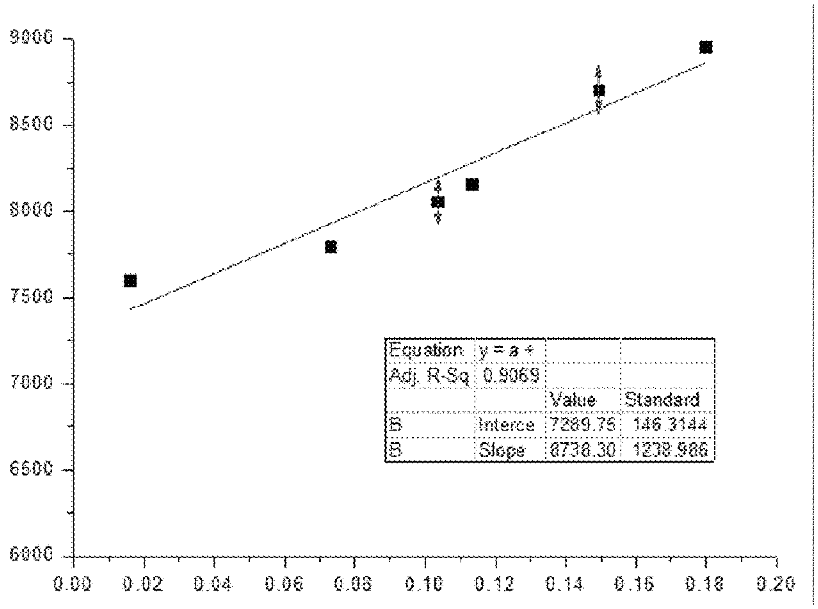
FIGS. 4A to 4D are "Lippert-Mataga plot" graphs.
Figure 4B:
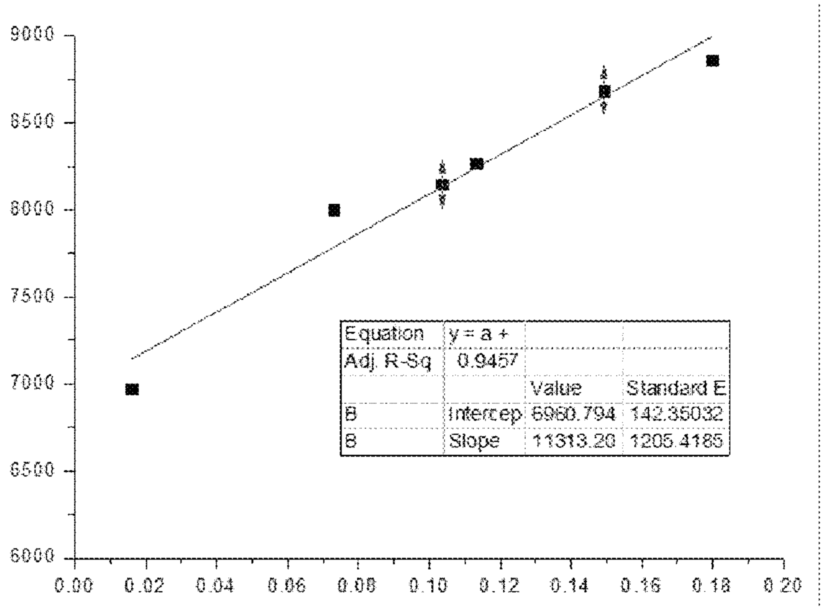

Referring to FIGS. 4A and 4B, which are "Lippert-Mataga plot" graphs of the compounds 1 and 2 (Com1 and Com2), the compounds 1 and 2 provide the linear relation ($R^2$>0.90). Namely, the compounds 1 and 2 provide the FADF emission where both the singlet exciton and the triplet exciton are engaged in the emission.

Figure 4C:
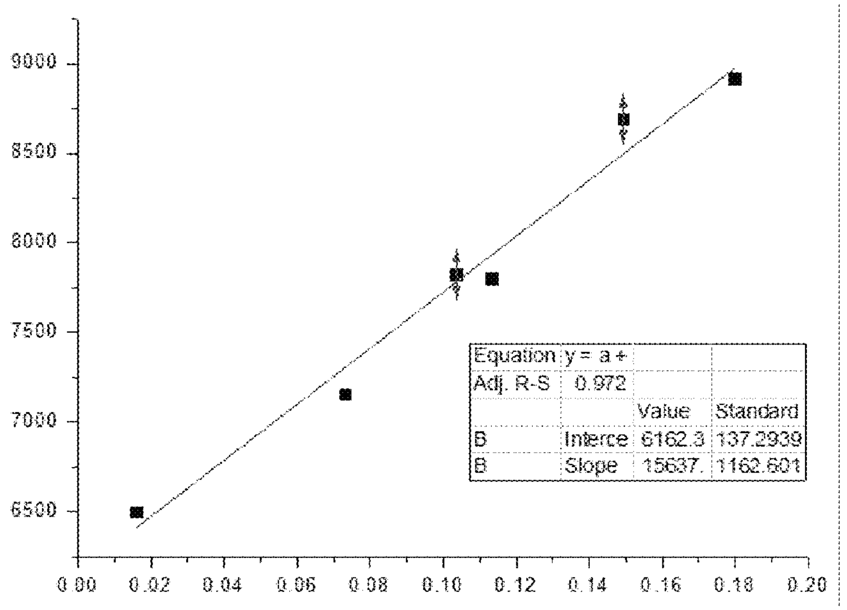

On the other hand, referring to FIG. 4C, which is "Lippert-Mataga plot" graphs of the reference compound 1 (Ref1) in Formula 5, the reference compound 1 also provides the linear relation. However, in the reference compound 1 (Ref1), since the charge is transferred through the bonding orbital of the molecule, the conjugation length is increased such that the red-shift problem is generated.

Figure 4D:
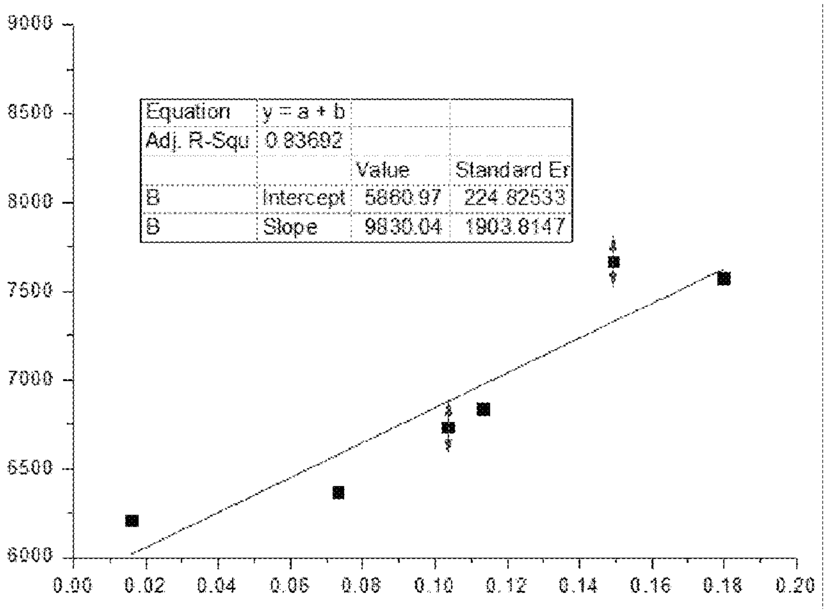

Referring to FIG. 4D, which is "Lippert-Mataga plot" graphs of the reference compound 2 (Ref2) in Formula 6, the reference compound 2 does not provide the linear relation. ($R^2$=0.83692) Namely, the reference compound 2 (Ref2) does not provide the FADF emission.

In the space-through charge transfer compound of the present invention, the 25% excitons in the singlet state and the 75% excitons in the triplet state are transited into the intermediate state by an outer force, i.e., a field generated when the OLED is driven. (Intersystem crossing) The excitons in the intermediate state are transited into the ground state such that the emitting efficiency is improved. Namely, in the fluorescent compound, since the singlet exciton and the triplet exciton are engaged in the emission, the emitting efficiency is improved.

OLED

An ITO layer is deposited on a substrate and washed to form an anode (3 mm*3 mm) The substrate is loaded in a vacuum chamber, and a hole injecting layer (40 Å, NPB (N,N'-di(naphthalen-1-yl)-N,N'-diphenyl-benzidine)), a hole transporting layer (10 Å, mCP (N,N'-Dicarbazolyl-3, 5-benzene)), an emitting material layer (200 Å, host (bis{2-[di(phenyl)phosphino]phenyl}ether oxide) and dopant (12%)), an electron transporting layer (300 Å, 1,3,5-tri (phenyl-2-benzimidazole)-benzene), an electron injecting layer (10 Å, LiF), and a cathode (Al) are sequentially formed on the anode under a base pressure of about $10^{-6}$ to $10^{-7}$ Torr.

(1) Example 1 (Ex1)

The compound 1 is used as the dopant to form the OLED.

(2) Example 2 (Ex2)

The compound 2 is used as the dopant to form the OLED.

(3) Example 3 (Ex3)

The compound 11 is used as the dopant to form the OLED.

(4) Example 4 (Ex4)

The compound 12 is used as the dopant to form the OLED.

(5) Example 5 (Ex5)

The compound 13 is used as the dopant to form the OLED.

(6) Example 6 (Ex6)

The compound 14 is used as the dopant to form the OLED.

(7) Comparative Example 1 (Ref1)

The reference compound 1 in the Formula 5 is used as the dopant to form the OLED.

(8) Comparative Example 2 (Ref2)

The reference compound 2 in the Formula 6 is used as the dopant to form the OLED.

TABLE 7

| | Voltage | Efficiency | | EQE | | |
|---|---|---|---|---|---|---|
| | (V) | Cd/A | Lm/W | (%) | CIE(X) | CIE(Y) |
| Ex1 | 4.3 | 6.1 | 4.4 | 6.8 | 0.142 | 0.092 |
| Ex2 | 4.5 | 6.4 | 4.5 | 6.9 | 0.143 | 0.089 |
| Ex3 | 4.2 | 9.2 | 6.9 | 9.7 | 0.157 | 0.136 |
| Ex4 | 4.4 | 8.8 | 6.3 | 9.2 | 0.149 | 0.127 |
| Ex5 | 4.3 | 6.7 | 4.9 | 7.0 | 0.148 | 0.097 |
| Ex6 | 4.4 | 7.3 | 5.2 | 8.1 | 0.151 | 0.103 |
| Ref1 | 4.7 | 5.9 | 3.9 | 6.3 | 0.142 | 0.203 |
| Ref2 | 4.6 | 4.2 | 4.2 | 4.7 | 0.144 | 0.091 |

As shown in Table 7, the OLEDs using the compounds of the present invention (Ex1 to Ex6) and the OLED using the reference compound 1 (Ref1) have improved efficiency. However, there is difference in the color purity. Namely, in comparison to the OLED using the reference compound 1 (Ref1), the OLEDs using the compounds of the present invention (Ex1 to Ex6) provide the deep blue image.

On the other hand, the OLEDs using the compounds of the present invention (Ex1 to Ex6) and the OLED using the reference compound 2 (Ref2) have similar color purity. However, there is difference in the emitting efficiency. Namely, in comparison to the OLED using the reference compound 2 (Ref2), the OLEDs using the compounds of the present invention (Ex1 to Ex6), which is the charge transfer complex, have excellent emitting efficiency.

Consequently, the OLED using the space-through charge transfer compound of the present invention has advantages in both the emitting efficiency and the color purity.

Figure 5:
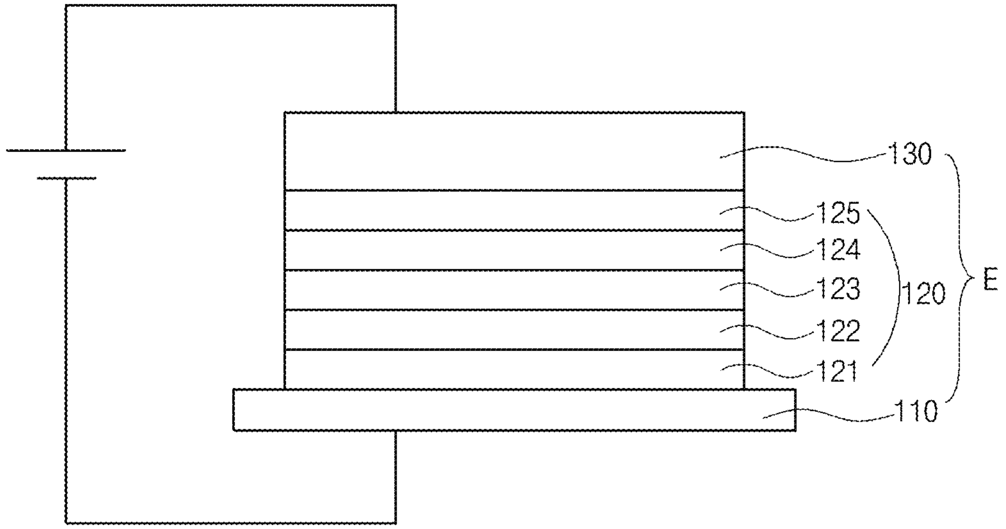
FIG. 5 is a schematic cross-sectional view of an organic light emitting diode (OLED) according to the invention.

FIG. 5 is a schematic cross-sectional view of an OLED according to the invention.

As shown in FIG. 5, the OLED "E" is formed on a substrate (not shown). The OLED "E" includes a first electrode 110 as an anode, a second electrode 130 as a cathode and an organic emitting layer 120 therebetween.

Although not shown, an encapsulation film, which includes at least one inorganic layer and at least one organic layer and covers the OLED "E", and a cover window on the encapsulation film may be further formed to form a display device including the OLED "E". The substrate, the encapsulation film and the cover window may have a flexible property such that a flexible display device may be provided.

The first electrode 110 is formed of a material having a relatively high work function, and the second electrode 130 is formed of a material having a relatively low work function. For example, the first electrode 110 may be formed of indium-tin-oxide (ITO), and the second electrode 130 may be formed of aluminum (Al) or Al alloy (AlNd). The organic emitting layer 120 may include red, green and blue emitting patterns.

The organic emitting layer 120 may have a single-layered structure. Alternatively, to improve the emitting efficiency, the organic emitting layer 120 includes a hole injection layer (HIL) 121, a hole transporting layer (HTL) 122, an emitting material layer (EML) 123, an electron transporting layer (ETL) 124, and an electron injection layer (EIL) 125 sequentially stacked on the first electrode 110.

At least one selected from the HIL 121, the HTL 122, the EML 123, the ETL 124, and the EIL 125 includes the space-through charge transfer compound in the Formula 1.

For example, the EML 123 may include the space-through charge transfer compound in Formula 1. The space-through charge transfer compound acts as the dopant, and the EML 123 may further include a host to emit the blue light. In this instance, the dopant has about 1 to 30 weight % with respect to the host.

A difference between the HOMO of the host "$HOMO_{Host}$" and the HOMO of the dopant "$HOMO_{Dopant}$" or a difference between the LUMO of the host "$LUMO_{Host}$" and the LUMO of the dopant "$LUMO_{Dopant}$" is less than 0.5 eV. ($|HOMO_{Host}-HOMO_{Dopant}|\leq 0.5$ eV or $|LUMO_{Host}-LUMO_{Dopant}|\leq 0.5$ eV) In this instance, the charge transfer efficiency from the host to the dopant may be improved.

The triplet energy of the dopant is smaller than the triplet energy of the host, and a difference between the singlet energy of the dopant and the triplet energy of the dopant is less than 0.3 eV. ($\Delta E_{ST}\leq 0.3$ eV) As the difference "$\Delta E_{ST}$" is smaller, the emitting efficiency is higher. In the space-through charge transfer compound of the present invention, even if the difference "$\Delta E_{ST}$" between the singlet energy of the dopant and the triplet energy of the dopant is about 0.3 eV, which is relatively large, the excitons in the singlet state "$S_1$" and the excitons in the triplet state "$T_1$" can be transited into the intermediate state "$I_1$".

For example, the host, which meets the above condition, may be selected from materials in Formula 7. (Bis[2-(diphenylphosphino)phenyl]ether oxide (DPEPO), 2,8-bis(diphenylphosphoryl)dibenzothiophene (PPT), 2,8-di(9H-carbazol-9-yl)dibenzothiophene (DCzDBT), m-bis(carbazol-9-yl)biphenyl (m-CBP), Diphenyl-4-triphenylsilylphenyl-phosphine oxide (TPSO1), 9-(9-phenyl-9H-carbazol-6-yl)-9H-carbazole (CCP) in order.)

[Formula 7]

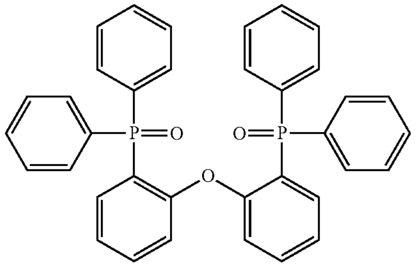

-continued

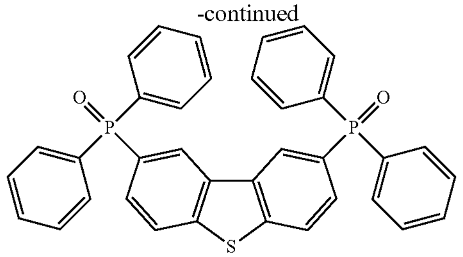

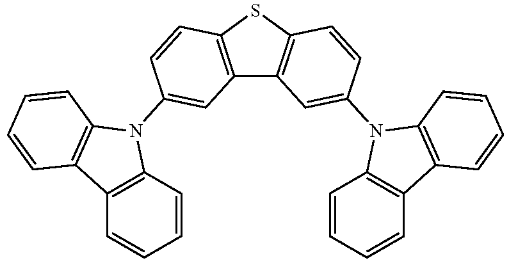

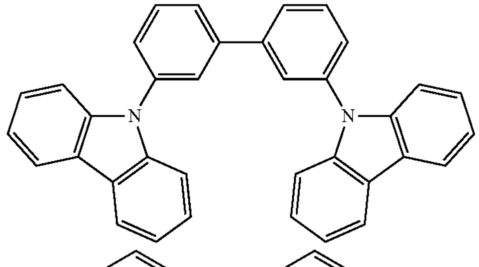

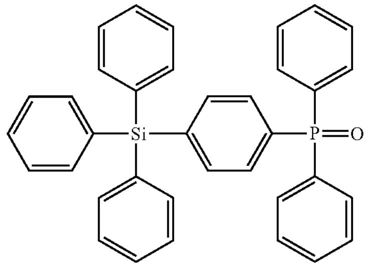

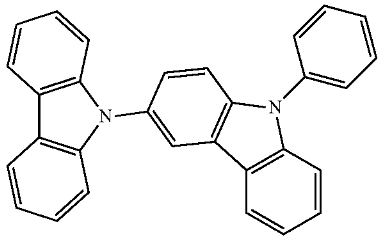

On the other hand, the space-through charge transfer compound of the present invention may act as a host in the EML 123, and the EML 123 may further include a dopant to emit the blue light. In this instance, the dopant has about 1 to 30 weight % with respect to the host. Since the development of the blue host having excellent properties is insufficient, the space-through charge transfer compound of the present invention may be used as the host to increase the degree of freedom for the host. In this instance, the triplet energy of the dopant may be smaller than the triplet energy of the host of the space-through charge transfer compound of the present invention.

The EML 123 may include a first dopant of the space-through charge transfer compound of the present invention, a host and a second dopant. The weight % summation of the first and second dopants may be about 1 to 30 to emit the blue light. In this instance, the emitting efficiency and the color purity may be further improved.

In this instance, the triplet energy of the first dopant, i.e., the space-through charge transfer compound of the present invention, may be smaller than the triplet energy of the host and larger than the triplet energy of the second dopant. In addition, a difference between the singlet energy of the first dopant and the triplet energy of the first dopant is less than 0.3 eV. ($\Delta E_{ST} \leq 0.3$ eV) As the difference "$\Delta E_{ST}$" is smaller, the emitting efficiency is higher. In the space-through charge transfer compound of the present invention, even if the difference "$\Delta E_{ST}$" between the singlet energy of the dopant and the triplet energy of the dopant is about 0.3 eV, which is relatively large, the excitons in the singlet state "$S_1$" and the excitons in the triplet state "$T_1$" can be transited into the intermediate state "$I_1$".

As mentioned above, in the space-through charge transfer compound of the present invention, since the electron donor moiety and the electron acceptor moiety are combined or linked in one molecule and the overlap between the HOMO and the LUMO is decreased, the space-through charge transfer compound of the present invention acts as a charge transfer complex such that the emitting efficiency of the compound is improved. Namely, in the space-through charge transfer compound of the present invention, the excitons in the triplet state are engaged in the emission such that the emitting efficiency of the compound is improved.

In addition, since the electron donor moiety and the electron acceptor moiety are combined or linked to the first and eighth positions of the naphthalene core, a space between the electron donor moiety and the electron acceptor moiety is decreased or minimized. Accordingly, the charge transfer is directly generated through the space between the electron donor moiety and the electron acceptor moiety such that the conjugation length is decreased. As a result, the red shift problem in the emitted light is prevented. Namely, the OLED using the space-through charge transfer compound of the present invention can emit the deep blue light. Accordingly, the OLED using the space-through charge transfer compound of the present invention has advantages in the emitting efficiency and the image quality.

It will be apparent to those skilled in the art that various modifications and variations can be made in the embodiment of the invention without departing from the spirit or scope of the invention. Thus, it is intended that the embodiment of the invention cover the modifications and variations of this invention provided they come within the scope of the appended claims and their equivalents.

What is claimed is:

1. A space-through charge transfer compound, comprising:

a naphthalene core;

an electron donor moiety selected from the group consisting of carbazole and phenylcarbazole; and an electron acceptor moiety selected from the group consisting of pyridine, diazine, triazole, and phenyl benzodiazole, wherein the electron donor moiety and the electron acceptor moiety are combined to first and eighth positions of the naphthalene core with a benzene linker, respectively.

2. A space-through charge transfer compound of Formula 1:

[Formula 1]

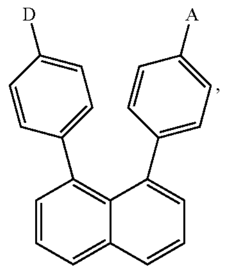

wherein D is selected from Formula 2, and A is selected from Formula 3:

[Formula 2]

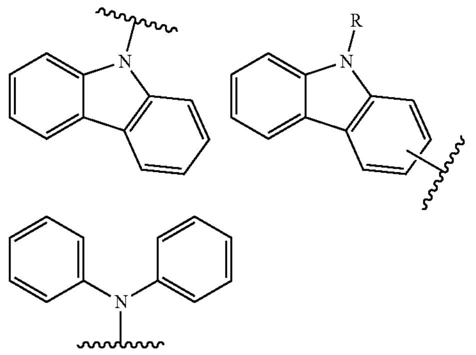

[Formula 3]

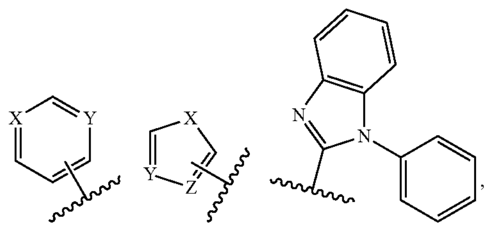

wherein R in the Formula 2 is selected from the group consisting of hydrogen, C1 alkyl through C8 alkyl, and C6 aryl through C20 aryl, and wherein X, Y, Z in the Formula 3 are independently selected from the group consisting of carbon and nitrogen, and at least one selected from X and Y is nitrogen.

3. The space-through charge transfer compound according to claim 2, wherein a difference between a singlet energy of the space-through charge transfer compound and a triplet energy of the space-through charge transfer compound is less than 0.3 eV.

4. An organic light emitting diode, comprising:

a first electrode;

a second electrode facing the first electrode; and an organic emitting layer between the first electrode and the second electrode, the organic emitting layer including a space-through charge transfer compound, wherein the space-through charge transfer compound includes a naphthalene core, an electron donor moiety selected from the group consisting of carbazole and phenylcarbazole, and an electron acceptor moiety selected from the group consisting of pyridine, diazine, triazole, and phenyl benzodiazole, and wherein the electron donor moiety and the electron acceptor moiety are combined to first and eighth positions of the naphthalene core with a benzene linker, respectively.

5. The organic light emitting diode according to claim 4, wherein the organic emitting layer includes a hole injection layer (HIL), a hole transporting layer (HTL), an emitting material layer (EML), an electron transporting layer (ETL), and an electron injection layer (EIL), and wherein at least one from selected from the group consisting of the HIL, the HTL, the EML, the ETL, and the EIL includes the space-through charge transfer compound.

6. The organic light emitting diode according to claim 4, wherein a difference between a singlet energy of the space-through charge transfer compound and a triplet energy of the space-through charge transfer compound is less than 0.3 eV.

7. The organic light emitting diode according to claim 4, wherein the organic emitting layer further includes a host, and the space-through charge transfer compound is used as a dopant.

8. The organic light emitting diode according to claim 7, wherein a difference between a highest occupied molecular orbital (HOMO) of the host and a HOMO of the dopant or a difference between a lowest unoccupied molecular orbital (LUMO) of the host and a LUMO of the dopant is less than 0.5 eV.

9. The organic light emitting diode according to claim 4, wherein the organic emitting layer further includes a dopant, and the space-through charge transfer compound is used as a host.

10. The organic light emitting diode according to claim 4, wherein the organic emitting layer further includes a host and a first dopant, and the space-through charge transfer compound is used as a second dopant, and wherein a triplet energy of the second dopant is smaller than a triplet energy of the host and larger than a triplet energy of the first dopant.

11. An organic light emitting diode, comprising:

a first electrode;

a second electrode facing the first electrode; and an organic emitting layer between the first electrode and the second electrode, the organic emitting layer including a space-through charge transfer compound of Formula 1:

[Formula 1]

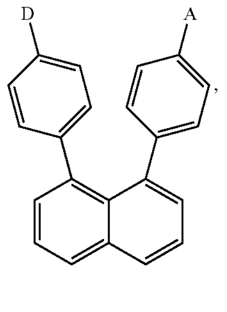

wherein D is selected from Formula 2, and A is selected from Formula 3:

[Formula 2]

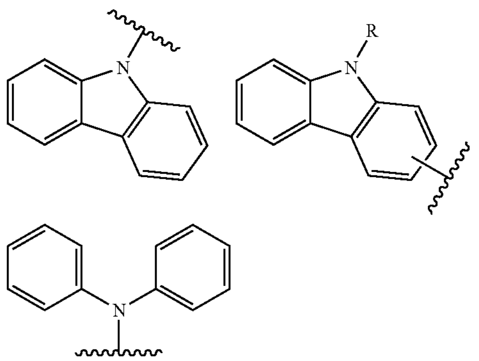

[Formula 3]

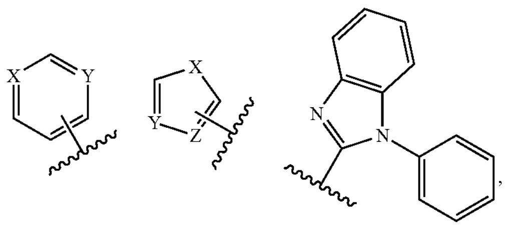

wherein R in the Formula 2 is selected from the group consisting of hydrogen, C1 alkyl through C8 alkyl, and C6 aryl through C20 aryl, and wherein X, Y, Z in the Formula 3 are independently selected from the group consisting of carbon and nitrogen, and at least one selected from X and Y is nitrogen.

12. The organic light emitting diode according to claim 11, wherein the organic emitting layer includes a hole injection layer (HIL), a hole transporting layer (HTL), an emitting material layer (EML), an electron transporting layer (ETL), and an electron injection layer (EIL), and wherein at least one from selected from the group consisting of the HIL, the HTL, the EML, the ETL, and the EIL includes the space-through charge transfer compound.

13. The organic light emitting diode according to claim 11, wherein a difference between a singlet energy of the space-through charge transfer compound and a triplet energy of the space-through charge transfer compound is less than 0.3 eV.

14. The organic light emitting diode according to claim 11, wherein the organic emitting layer further includes a host, and the space-through charge transfer compound is used as a dopant.

15. The organic light emitting diode according to claim 14, wherein a difference between a highest occupied molecular orbital (HOMO) of the host and a HOMO of the dopant or a difference between a lowest unoccupied molecular orbital (LUMO) of the host and a LUMO of the dopant is less than 0.5 eV.

16. The organic light emitting diode according to claim 11, wherein the organic emitting layer further includes a dopant, and the space-through charge transfer compound is used as a host.

17. The organic light emitting diode according to claim 11, wherein the organic emitting layer further includes a host and a first dopant, and the space-through charge transfer compound is used as a second dopant, and wherein a triplet energy of the second dopant is smaller than a triplet energy of the host and larger than a triplet energy of the first dopant.

18. A display device, comprising:

a substrate;

an organic light emitting diode on the substrate and including a first electrode, a second electrode facing the first electrode, and an organic emitting layer between the first electrode and the second electrode, the organic emitting layer including a space-through charge transfer compound;

an encapsulation film on the organic light emitting diode; and a cover window on the encapsulation film, wherein the space-through charge transfer compound includes a naphthalene core, an electron donor moiety selected from the group consisting of carbazole and phenylcarbazole, and an electron acceptor moiety selected from the group consisting of pyridine, diazine, triazole, and phenyl benzodiazole, and wherein the electron donor moiety and the electron acceptor moiety are combined to first and eighth positions of the naphthalene core with a benzene linker, respectively.

19. A display device, comprising:

a substrate;

an organic light emitting diode on the substrate and including a first electrode, a second electrode facing the first electrode and an organic emitting layer between the first electrode and the second electrode, the organic emitting layer including a space-through charge transfer compound of Formula 1;

an encapsulation film on the organic light emitting diode; and a cover window on the encapsulation film,

[Formula 1]

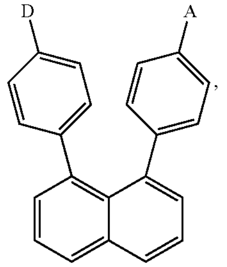

wherein D is selected from Formula 2, and A is selected from Formula 3:

[Formula 2]

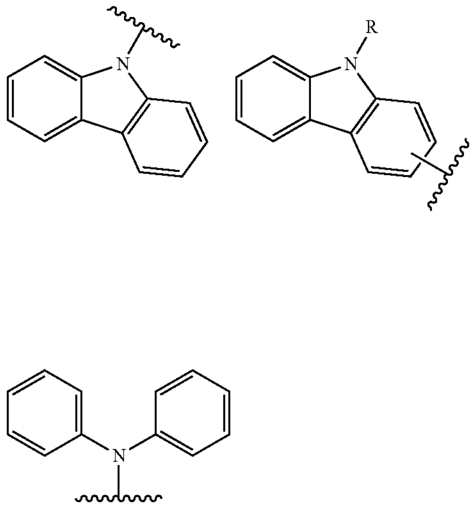

[Formula 3]

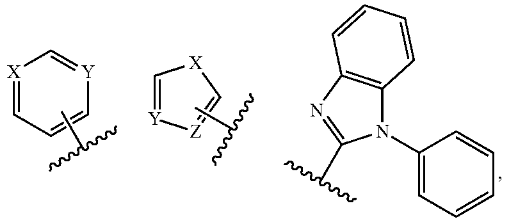

wherein R in the Formula 2 is selected from the group consisting of hydrogen, C1 alkyl through C8 alkyl, and C6 aryl through C20 aryl, and wherein X, Y, Z in the Formula 3 are independently selected from the group consisting of carbon and nitrogen, and at least one selected from X and Y is nitrogen.

* * * * *